(12) United States Patent
Bazin et al.

(10) Patent No.: US 6,541,611 B1
(45) Date of Patent: Apr. 1, 2003

(54) LO-CD2B ANTIBODY

(75) Inventors: Hervé Bazin, Brussels (BE); Dominique Latinne, Brussels (BE); Pierre Gianello, Rixensart (BE)

(73) Assignee: Universite Catholique de Louvain, Louvain-la-Neuve (BE)

( * ) Notice: Subject to any disclaimer, the term of this patent is extended or adjusted under 35 U.S.C. 154(b) by 0 days.

(21) Appl. No.: 09/593,830

(22) Filed: Jun. 14, 2000

Related U.S. Application Data

(60) Provisional application No. 60/139,955, filed on Jun. 18, 1999, and provisional application No. 60/146,038, filed on Jul. 28, 1999.

(51) Int. Cl.[7] .......................... C07K 16/28; C12N 5/12
(52) U.S. Cl. ..................... 530/388.75; 530/387.1; 530/388.1; 530/388.2; 530/388.22; 530/388.7; 530/388.73; 435/326; 435/332; 435/334; 435/343; 435/343.1; 435/343.2; 435/346
(58) Field of Search ................... 435/326, 343, 435/346; 530/387.1, 388.22, 388.75

(56) References Cited

U.S. PATENT DOCUMENTS

| | | | |
|---|---|---|---|
| 5,730,979 A | 3/1998 | Bazin et al. .............. | 424/154.1 |
| 5,817,311 A | 10/1998 | Bazin et al. .............. | 424/154.1 |
| 5,951,983 A | 9/1999 | Bazin et al. .............. | 424/154.1 |

FOREIGN PATENT DOCUMENTS

| | | |
|---|---|---|
| WO | WO90/01752 | 7/1990 |
| WO | WO91/01752 | 2/1991 |

OTHER PUBLICATIONS

Berlin et al. Transplantation 53:840–849 (1992).*
Denning, Leucocyte Typing V, vol. 1, ED.Schlossman et al. oxford university Press pp. 342–343, 1995.*
Arulanandum et al. in Levcocyte Typing V, vol. 1, pp. 344–345 (ED.) Schlossman et al. Oxford University Press, 1995.*
Bow Den et al in Levcocyte Typing V, vol. 1, pp. 346–347 (ED.) Schlossman et al. Oxford University Press 1995.*
Aliessandra et al. in Levcocyte Typing V vol. 1, pp. 347–348. (ED.) Schlossman et al. Oxford University Press, 1995.*
Kato in Leucocyte Typing V1, pp. 39–43 (ED.) Kishimoto et al. Garaud Publishing Inc. 1998.*
Jonker, et al., *Transplantation Proceedings*, vol. 15, No. 1, pp. 635–638 (Mar. 1983).
Remlinger, et al., *Human Immunology*, vol. 9, pp. 21–35 (1984).
Martin, et al., *Transplantation Proceedings*, vol. 16, No. 6 (Dec. 1984).
Jonker, et al., *Transplantation*, vol. 45, No. 4, pp. 677–682 (Apr. 1988).
Trinchieri, *Advances in Immunology*, vol. 47, pp. 272–303 (1989).
Auchindoss, et al., *Fundamental Immunology*, Paul, ed., Raven Press Ltd., New York, pp. 889–922 (1989).
Sharabi, et al., *J. Exp. Med.*, vol. 172, pp. 195–202 (Jul. 1990).
Bollinger, et al., *Transplantation Proceedings*, vol. 23, No. 1, pp. 587–588 (Feb. 1991).
DeLaParra, et al., *Belg. J. Zoology*, vol. 121, Supp. 1, p. 13 (Nov. 1991).
Berlin, et al., *Transplantation*, vol. 53, No. 4, pp. 840–849 (Apr. 1992).
Eddington, et al., *Biotechnology*, vol. 10, pp. 383–389 (Apr. 1992).
Kahan, *Curr. Opin. in Immunol.*, vol. 4, pp. 553–560 (Aug. 1992).
Monaco, *Immunomethods*, vol. 2, pp. 159–170 (1993).
Berzofsky, et al., *Fundamental Immunology*, Paul, ed., Raven Press Ltd, New York, p. 242 (1993).
Harris, et al., *Tibtech*, vol. 11, pp. 42–44 (Feb. 1993).
Rebellato, et al., *Transplantation Proceedings*, vol. 25, No. 1, pp. 598–599 (Feb. 1993).
Emery, et al., *Exp. Opin. Invest. Drugs*, vol. 3, No. 3, pp. 241–251 (1994).

\* cited by examiner

*Primary Examiner*—Phillip Gambel
(74) *Attorney, Agent, or Firm*—Elliot M. Olstein; Raymond J. Lillie

(57) ABSTRACT

A monoclonal antibody which binds to baboon and human CD2, and in particular LO-CD2b antibody. The antibody may be employed to prevent and inhibit an immune response in human patients, such as when the immune response is mediated by the activation and proliferation of T-cells or natural killer cells.

2 Claims, 12 Drawing Sheets

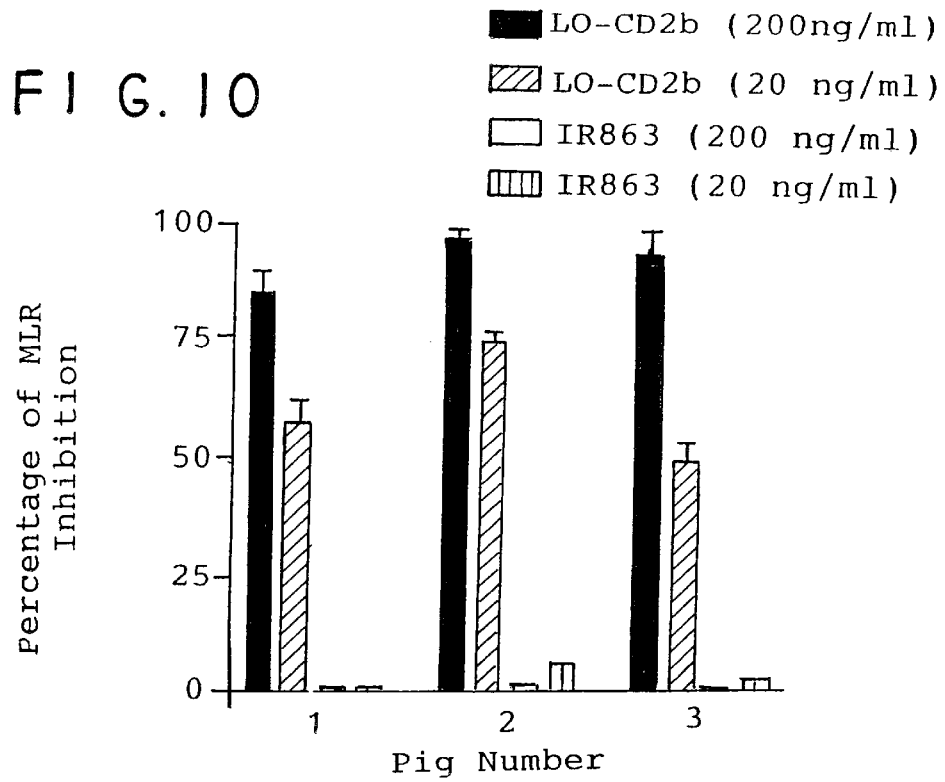
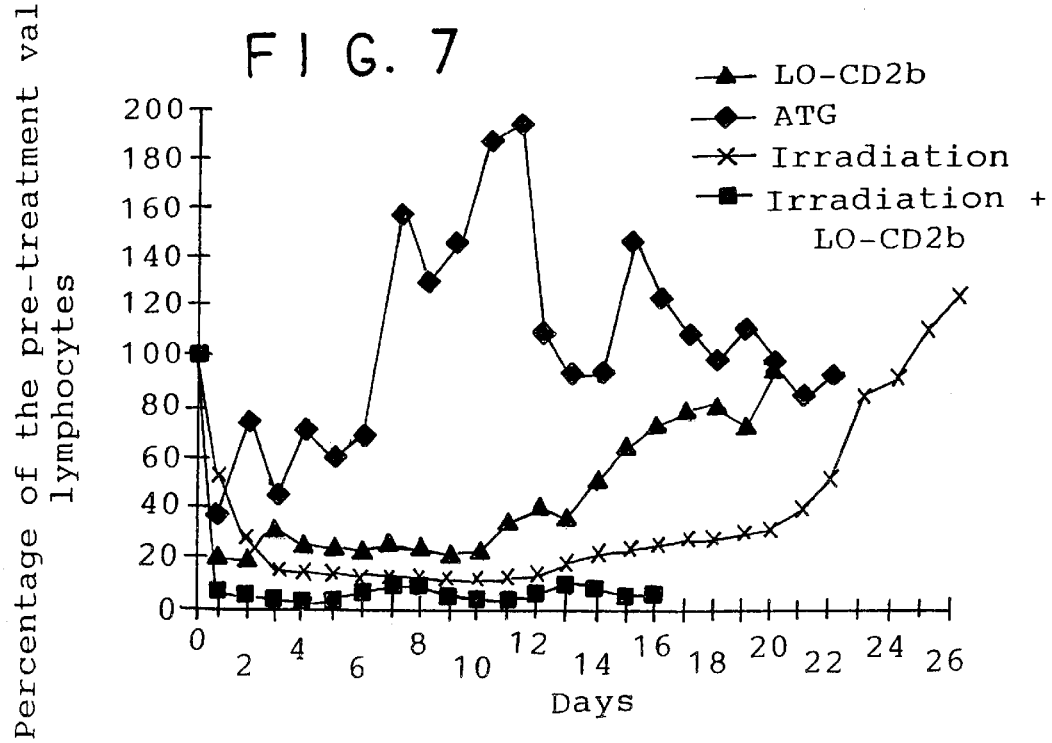

LO-CD2B ANTIBODY

This Application claims priority based on, and is a continuation in part of provisional application Ser. No. 60/139,955, filed Jun. 18, 1999, and of provisional application Ser. No. 60/146,038, filed Jul. 28, 1999.

This invention relates to an antibody (or fragment or derivative thereof) and preferably, to an antibody (or fragment or derivative thereof) which binds to human lymphocytes. More particularly, this invention relates to preventing and/or inhibiting on-going immune responses in a patient through the administration of such antibody (or fragment or derivative thereof) to a patient. Preferably, this invention relates to preventing or inhibiting T cell activation and proliferation through the administration of such antibody or fragment or derivative thereof to a patient.

The establishment of donor-specific immunological tolerance to primarily vascularized allografts would obviate the use of chronic immunosuppressive drug therapy and the associated morbidity and mortality. The main hurdle in developing tolerance protocols for use in humans is to determine the least toxic but consistently successful immunosuppressive regimens. It is therefore of overwhelming importance to establish experimental models, especially large animal models which will reliably be predictive of use in the clinical setting. Outbred primates seem to be the most appropriate clinical relevant model, and central tolerance induction to primarily vascularized renal allografts has been previously reported in cynomolgus monkeys. (Kawai, et al., *Transplantation*, Vol. 59 pg. 256 (1995); Kimikawe, *Transplantation*, Vol. 64, pg. 709 (1997)). Tolerance induction in this model was based on development of mixed hematopoietic chimerism and was obtained by concomitant donor bone marrow infusion, non-myeloablative total body irradiation (3 Gy) and an immunosuppressive regimen including transient injection of rabbit anti-human thymocyte globulins and cyclosporin. Other models of tolerance induction in primates including post-transplant transient depletion of peripheral T cells with rabbit anti-thymocyte globulins and subsequent infusion of donor bone marrow and total lymphoid irradiation have been reported. (Carver, et al., *Transplant Proc.*, Vol. 23, pg. 480 (1991)). Mixed chimerism seems to be the key for central tolerance induction, but devplopment of microchimerism requires, at least, non lethal myeloablative irradiation combined with T cell-depleting agents, as tolerance seems to be favored by a milieu with minimally reactive T cells. (Contreras, et al., *Transplantation*, Vol. 65, pg. 1159 (1998)). The use of high doses of total irradiation in the clinical setting is, however, hazardous, especially in children, and efforts must be made in order to establish immunosuppressive protocols using easily monitorable T cell-depleting reagents that result in central tolerance and microchimerism as previously discovered in rodent studies. (Sykes, et al., *Nature Medicine*, Vol. 3, pg. 783 (1997)).

Recent studies showed that tolerance to primarily vascularized allografts in primates might be induced without irradiation, by using a new anti-CD3 immunotoxin (Contreras, et al. 1998). This very powerful T-cell depleting agent was used in conjunction with donor lymphohematopoietic cell infusion in order to produce a high level of chimerism (Contreras, et al. 1998; Knechtle, et al., *Transplantation*, Vol. 63, pg. 1 (1997); Thomas, et al., *Transplantation*, Vol. 64, pg. 124 (1997)). The profound and long-lasting T-cell depletion in both peripheral blood and lymph nodes may, however, limit its clinical applicability. In addition, the pre-existence of an immune agent against the diphtheria toxin moiety of the anti-CD3 immunotoxin could reduce the efficiency of this agent. Nonetheless, this molecule clearly demonstrates that central tolerance induction might be achievable in primate models without total body irradiation.

As of this time, there are no available immunosuppressive agents other than anti-CD3 immunotoxin which might produce such a strong peripheral and lymphoid T cell depletion in humans. Nonetheless, the Campath-1 mAb has been used in human clinical trials for bone marrow transplantation and provided a high incidence of mixed chimerism and encouraging results have been reported in renal allografts using this mAb. (Friend, *Ann. Acad. Med. Singapore*, Vol. 20, pg. 503 (1991); Nagler, et al., *Bone Marrow Transplantation*, Vol. 18, pg. 475 (1996); Friend, et al., *Transplantation*, Vol. 48, pg. 248 (1989); Hamilton, et al., *Bone Marrow Transplantation*, Vol. 17, pg. 819 (1996)). Recently, another mAb (LO-CD2a/BTI-322) has shown interesting T cell-depleting effects in humans. LO-CD2a/BTI-322, which is an anti-human CD2 mAb has demonstrated great efficiency in preventing acute cellular rejection in renal transplantation (Mourad, et al., *Transplant. Proc.*, Vol. 29, pg. 2353 (1991)), in graft versus host disease and liver transplantation (manuscript in preparation). This mAb, however, does not react with primate T cells, except for human and chimpanzee T cells and therefore cannot be used in experiments involving baboons and cynomolgus monkeys.

DETAILED DESCRIPTION

In accordance with the present invention, there is provided a monoclonal antibody or fragment thereof that recognizes both baboon and human CD2+ cells. As the CD2 molecule is expressed on all subsets of T cells including CD2 natural killer (NK) cells, LO-CD2b may be used as an immunotherapeutic reagent as well as providing a powerful tool for studies on optimizing conditioning regimens.

More particularly, in accordance with an aspect of the present invention, there is provided a molecule (preferably a monoclonal antibody or fragment thereof) which binds to the same epitope (or a portion thereof) on human lymphocytes as the monoclonal antibody produced by the cell line deposited as ATCC Deposit No. PTA-802. The antibody which is produced by the deposited cell line is hereinafter sometimes referred to as LO-CD2b. The term "molecule" or "antibody that binds to the same epitope as LO-CD2b" includes LO-CD2b. The term "LO-CD2b" includes the antibody produced by the deposited cell line and those identical thereto which may be produced, for example, by recombinant technology.

The molecules or antibodies of the present invention inhibit human T-cell activation and proliferation and Applicant has found that such inhibition can be effected when adding the molecule or antibody either before or after an agent which stimulates T-cell activation.

The molecules or antibodies of the present invention have the characteristics of binding to an epitope of a CD2 antigen (CD2 positive human T-cells) but it is to be understood, however, that the ability of such molecules or antibodies to inhibit T-cell activation or proliferation may or may not be effected through binding to CD2 positive cells, although Applicant presently believes that the mechanism of action involves binding of the molecule or antibody to CD2 positive cells.

In accordance with another aspect of the present invention there is provided a method of preventing and/or inhibiting on-going immune response in human patients through the administration to the patient of an antibody, hereinafter referred to as LO-CD2b (or fragment or derivative thereof) or any molecule that mimics such antibody or derivative or fragment thereof.

A cell line which produces LO-CD2b, was deposited on Jun. 22, 1999, at the American Type Culture Collection, 10801 University Blvd., Manassas, Va. 20110-2209, and was given the ATCC accession number PTA-802. Such antibody is a rat monoclonal antibody.

Although Applicants do not want to limit the invention to any theoretical reasoning, it is believed that the mechanism which enables the monoclonal antibody of this invention to prevent or reduce the severity of an immune response, and to inhibit the activation and proliferation of T-cells, is the fact that the LO-CD2b antibody either decreases the density of CD2 expressed on T cell surfaces and thus decreases the number of $CD2^+$ T lymphocytes; and/or affects signal transduction. It is believed that these mechanisms of action are responsible for not only the prevention of immune response, but also the reduction in severity of on-going immune responses.

In accordance with an aspect of the present invention there is provided a process for inhibiting initial or further activation and proliferation of T cells in a human patient by administering to the patient an effective amount of a molecule (preferably an antibody) which binds to the same epitope (or any part thereof) on human lymphocytes as the LO-CD2b antibody. The preferred molecule is LO-CD2b or a chimeric and/or humanized form thereof. Such a molecule would, for example, contain the same complementarity determining region (CDR) as the LO-CD2b antibody.

The term "inhibit" as used herein throughout this Applicant is intended to mean prevention, or inhibition, or reduction in severity, or induction of tolerance to, or reversal of graft rejection. The term "graft" as used herein for purposes of this application shall mean any and all transplantation, including but not limited to, allograft and xenograft transplantation. Such transplantation may by way of example include, but not be limited to, transplantation of cells, bone marrow, tissue, solid-organ, bone, etc.

The term "immune response(s)" as used herein is intended to mean immune responses dependent upon T cell activation and proliferation which includes both cellular effects and T cell dependent antibodies which may be elicited in response to, by way of example and not limitation: (i) grafts, (ii) graft versus host disease, and (iii) autoantigens resulting in autoimmune diseases, which by way of example include but are not limited to rheumatoid arthritis, systemic lupus, multiple sclerosis, diabetes mellitus, etc.

The molecule employed in the present invention is one which binds to the same epitope (or a part of that epitope) as the LO-CD2b monoclonal antibody. The term "binds to the same epitope as LO-CD2b monoclonal antibody" is intended to describe not only the LO-CD2b monoclonal antibody but also describes other antibodies, fragments or derivatives thereof or molecules which bind to the same such epitope as the LO-CD2b monoclonal antibody.

Such other antibodies include by way of example and not limitation rat, murine, porcine, bovine, human, chimeric, humanized antibodies, or fragments or derivatives thereof.

The term "derivative" as used herein means a chimeric or humanized antibody, single chain antibody, bispecific antibody or other such antibody which binds to the same epitope (or a portion thereof) as recognized by the LO-CD2b monoclonal antibody.

The term "fragment" as used herein means a portion of an antibody, by way of example such portions of antibodies shall include but not be limited to CDR, Fab, or such other portions, which bind to the same epitope or any portion thereof as recognized by LO-CD2b.

The term "antibody" as used herein includes polyclonal, monoclonal antibodies as well as antibody fragments, derivatives as well as antibodies prepared by recombinant techniques, such as chimeric or humanized antibodies, single chain or bispecific antibodies which bind to the same epitope or a portion thereof as recognized by the monoclonal antibody LO-CD2b. The term "molecules" includes by way of example and not limitation, peptides, oligonucleotides or other such compounds derived from any source which mimic the antibody or binds to the same epitope or a portion thereof as the antibody fragment or derivative thereof.

Another embodiment of the present invention provides for a method of treating a patient who is to receive or has received a graft transplant with an effective amount of at least one member selected from the group consisting of LO-CD2b antibody, or an antibody, or derivative or fragment thereof or molecules which bind to the same epitope (or a portion thereof) as the LO-CD2b antibody. The treatment is preferably effected with the whole or intact LO-CD2b antibody.

A monoclonal antibody of this invention as hereinabove described may be produced by techniques known in the art such as described by Kohler and Milstein (Nature 256, Pg. 495–497, 1975) as well as the techniques disclosed herein. The preparation of a monoclonal LO-CD2b antibody is described in more detail in Example 1 of this Application. As hereinabove indicated LO-CD2b antibodies may also be produced by recombinant techniques using procedures known in the art. The recombinant antibody may also be in the form of a chimeric antibody wherein the variable regions of a LO-CD2b rat antibody are combined with the constant region of an antibody of another species. Thus, for example, the monoclonal antibody may be humanized by combining the CDR regions of a rat LO-CD2b monoclonal antibody with the V region frameworks and constant regions of a human antibody to provide a chimeric human-rat monoclonal antibody.

In one embodiment, the antibody is a humanized form of LO-CD2b antibody constructed from the constant regions of a human antibody, and the framework and CDR regions of the light and heavy chain variable regions, in which the framework regions of the light and heavy chain variable regions are derived from the framework regions of the light and heavy chain variable region of a human antibody, and the CDR's are the rat LO-CD2b CDR's. In one embodiment, one or more amino acid residues of the framework regions of the light and heavy chain variable regions may be amino acid residues from the rat LO-CD2b framework regions. Such residues from the rat framework regions are retained in the humanized antibody because such residues may maintain the binding specificity of LO-CD2b. Thus, in producing a humanized antibody, in accordance with a preferred aspect of the invention the CDR's of a human antibody are replaced with the CDR's of LO-CD2b with the added factor that certain amino acids of the light chain variable portion of LO-CD2b in particular from FR1, FR2 and FR3 and certain amino acids of the heavy chain variable portion of LO-CD2b in particular from FR-2 and FR-3 are retained in constructing the humanized antibody; i.e., the corresponding. amino acids of the human framework are replaced with the noted amino acids from the rat LO-CD2b framework.

In another embodiment, the present invention is related to a chimeric antibody comprised of a human constant region and the variable regions from rat LO-CD2b and to the use thereof.

The preparation of LO-CD2b monoclonal antibody suitable for the purposes of the present invention should be apparent to those skilled in the art from the teachings herein.

An antibody or fragment or derivative thereof or molecule of the type hereinabove described may be administered in vivo in accordance with the present invention to inhibit the activation and proliferation of T-cells, and decrease the density of CD2 expression on the cell surface and thereby reduce the number of $CD2^+$ T lymphocytes.

Thus, for example, in an in vivo procedure, such LO-CD2b antibodies are administered to prevent and/or inhibit immune response and thereby inhibit T cell activation and proliferation.

An antibody or fragment or derivative thereof or molecule of the type herein above described may be administered ex vivo in accordance with the present invention to decrease the density of $CD2^+$ expression on the cell surface and thus reduce the number of $CD2^+$ cells of the donor cells. By way of example and not limitation, in an ex vivo procedure, such antibodies or fragments or derivatives thereof or molecules would be infused into donor bone marrow prior to transplantation to prevent the onset of graft versus host disease upon transplantation.

In such an in vivo or ex vivo technique, the antibody or fragment or derivative thereof or molecule will be administered in a pharmaceutically acceptable carrier. As representative examples of such carriers, there may be mentioned normal saline solution, buffers, etc. Such pharmaceutical carriers are well known in the art and the selection of a suitable carrier is deemed to be within the scope of those skilled in the art from the teachings contained herein.

The LO-CD2b antibody or other molecule of the present invention may be administered in vivo intravenously or by intramuscular administration, etc.

As herein above indicated, LO-CD2b antibody or other molecule of the present invention is administered in vivo in an amount effective to inhibit graft rejection. The term "an effective amount" for purposes of this Application shall mean that amount of monoclonal antibody capable of producing the desired effect, i.e., the inhibition of graft rejection or inhibition of the activation of T-cells. In general, such antibody is administered in an amount of at least 1 mg. It is to be understood that lower amounts could be used. In addition after the initial treatment, the herein above described amounts may be reduced for subsequent treatments, if any. Thus the scope of the invention is not limited by such amounts.

In accordance with the present embodiment, such antibodies are administered in order to maintain the inhibition of T-cell activation and graft rejection. Thus, by way of example and not limitation, the antibody may be administered by intravenous infusion over a one to two hour period in amount of from about 1 mg/dose to about 50 mg/dose in a physiologically acceptable carrier suspension once or twice a day for a period of from about eight. days or more, as needed. Such treatment for graft rejection is preferably started at, or immediately prior to, or shortly after transplantation or when graft rejection occurs. The treatment could be given once or twice a day for as little as one or two days when. started at the time of transplantation to induce a selective hyporesponsive state to the transplant. Such treatment for autoimmune diseases with respect to the administration of the antibody or fragment or derivative thereof or molecule in accordance with the present invention is begun when the attending physician has determined it is desirable to inhibit a pathological immune response.

Thus, in accordance with an aspect of the present invention, by administering an antibody in accordance with the invention at the time of transplantation and in most cases for a short period thereafter there can be induced a hyporesponsiveness to the transplanted tissue or organ, thereby to prevent or inhibit further episodes of rejection.

The techniques of the present invention for inhibiting the activation of T-cells may be employed alone or in combination with other techniques, drugs or compounds for inhibiting the activation of T-cell or inhibiting graft rejection or graft versus host disease.

The invention will be further described with respect to the following examples, which are illustrative and which are not intended to limit the scope of the invention.

The cells, cultures, mAbs and mitogens used in the examples may be prepared and used by processes and procedures known and practiced in by those of ordinary skill in the art. The following are examples of processes or procedures that may be used for the preparation and use of the cells, cultures, mAbs and mitogens used in the examples which follow.

The purpose of the studies shown in Examples 1 through 6 was to determine whether LO-CD2b could inhibit human and nonhuman primate immune response in vitro and nonhuman immune response in vivo. The in vivo T cell depletion was therefore assessed in both peripheral blood and lymph nodes. In addition to being a strong immunosuppressive agent in vitro, LO-CD2b demonstrated-the ability to prolong a renal allograft survival.

EXAMPLES

The invention now will be described with respect to the following examples; however, the scope of the present invention is not intended to be limited thereby.

Example 1

Production of LO-CD2b

The LO-CD2b hybridoma was produced by the fusion of splenocytes from LOU/C rat 1 immunized with human purified T cells and the non-secreting rat fusion cell line IR983F (Bazin, 1992, Production of rat monoclonal antibodies with LOU rat non-secreting IR983F myeloma cell line, in *Protides of the biological fluid*, ed. H Peeters. Oxford: Pergamon Press). Purified human T lymphocytes ($5\times10^7$) were injected intraperitoneally into LOU/C rat two times at three week intervals. Fusion between the splenocytes from the immunized rat and the cell line was carried out four days after the second sensitization. The monoclonal antibody was produced in ascitic fluid and purified as previously described (Bazin et al. 1990, Purification of rat monoclonal antibodies from ascitic fluid, serum or culture supernatant, in *Rat hybridomas and Rat monoclonal antibodies*, ed. Bazin. Boca Raton, Fla.: CRC Press. Cell culture, cloning, isotyping and cell staining were performed as previously reported (Xia et al. 1990, Rat monoclonal antibodies specific for human T lymphocytes, in *Rat hybridomas and Rat monoclonal antibodies*, ed. Bazin. Boca Raton, Fla.: CRC Press).

Example 2

LO-CD2b Recognizes $CD2^+$ Cells

As evidenced by FC, E-rosetting and western blotting, LO-CD2b mAb interacts with the CD2 molecule on PBMC.

Inhibition of E-rosetting. After LSM purification (International Medical, Brussels, Belgium), 10×10$^6$ cells/ml of peripheral blood mononuclear cells (PBMCs) were suspended in MLR medium : AIM medium (Gibco, Verviers, Belgium) supplemented with 0.1 mM minimum essential medium (MEM, Gibco), 1 mM sodium pyruvate (Gibco), 20 M 2-mercaptoethanol, 2. mM L-glutamine, (Gibco), 100 μg/ml penicillin, (Gibco), 100 μg/ml streptomycin and 2% decomplemented (56° C., 0.5 h) baboon serum. These cells were then incubated with either LO-CD2b or LO-DNP57 (IgG2b, isotype control) at a concentration of 10 μg/ml. After a 30 minutes incubation, the cells were washed two times with phosphate-buffered saline (pH 7.2) (PBS) containing 2% fetal calf serum (FCS) and centrifuged (10 minutes, 400 g). The concentrated cells were then suspended in 1 ml of PBS and incubated for one hour with 2 ml of sheep red blood cells (SRBC) previously treated for 15 minutes at 37° C. with a solution of 2-aminoethylisothiouronium bromide (pH 9) (AET) solution. After washing, the supernatant was removed and the pellet suspended in 3 ml PBS. Three ml of LSM were then added and the solution centrifuged for 20 minutes at 750 g. The pellet was recovered and washed in PBS containing 2% FCS. The rosette formation was assessed by observing an aliquot under the microscope. The number of rosettes were calculated for 100 cells.

LO-CD2b blocked E-rosetting at a average of 90.6+2.6% (three experiments: 93.4%, 88.2% and 90.2%) with a mean of 5 rosettes/100 cells for LO-CD2b coated cells and 55 rosettes/100 cells for LO-DNP57.

Flow cytometry. In order to study the possible competition between LO-CD2b and other well-characterized anti-CD2 monoclonal antibodies such as T11 (Coulter® 660-23-89) or Leu5b (Becton Dickinson® 347–593) two experiments were performed. In the first experiment, baboon PBMCs isolated from 5 ml of heparinized blood by gradient centrifugation on LSM were suspended simultaneously with 5 μg/ml of fluoresceinated Leu5b or T11 and serial dilutions of LO-CD2b (from 5 μg/ml to 18 ng/ml). After a 30 minutes incubation and three washes, the percentage of cells labeled with fluorescein was assessed by flow cytometry (FC). In the second experiment, the baboon PBMCs were suspended with serial dilutions of LO-CD2b (10 μg/ml to 19 ng/ml) and a fluoresceinated mouse anti-rat IgG2b. After a 30 minutes of incubation and three washes, 10 μg/ml of Rhodamine labeled T11 (Coulter® 660-28-68) were added to each of the diluted LO-CD2b samples. The percentage of single or double positive cells was then assessed by FC.

In both assays, the decrease of LO-CD2b concentration by serial dilutions was concomitant with a significant and progressive increase of the percentage of cells labeled with rhodamine-T11 and fluorescein Leu5b anti-CD2 mAb (FIG. 1). There was a partial competition between LO-CD2b and T11 or Leu5b for the same surface molecule. This result suggested that LO-CD2b, Leu5b and T11 recognized a closely associated epitope on CD2$^+$ cells.

Western blot. PBMCs were isolated from 40 ml of baboon heparinized blood by density gradient centrifugation on LSM. Isolated PBMCs (125×10$^6$ cells diluted in 100 μl RPM1 buffer) were suspended overnight with 200 μl of lysis buffer (0.25M Tris pH 7.5; TRITON® 5%; NP-40® 5%, dilution 10x) and with protease inhibitors (pepstatin 0.1 mg/ml; leupeptin 1 mg/ml and phenyl-methylsulfonylfluoride 0.1 M) at a ratio of 1/100 After centrifugation, 25 μl, of supernatant was placed on a Bis-Tris-HCl buffered (pH6.4) polyacrylamide gel (NUPAGE™, NOVEX, San Diego, USA) under reducing conditions and transferred to a nitrocellulose membrane (NOVEX, San Diego, USA). After blocking with 1% skimmed milk (Merck, Darmstadt, Germany), the blot was incubated overnight with LO-CD2b diluted at 1:20,000 in PBS. After washing three times in PBS TWEEN® buffer, the blot was incubated for one hour at 4° C. with $^{125}$I-anti-rat sheep red blood cells diluted 1: 100 in PBS (Amersham Int. UK, 50/μCi/0.6ml). After incubation for one hour at 40° C., the blot was then washed with PBS TWEEN® buffer and autoradiographed. A rat anti-CD2 and a mouse anti-rat IgG2b were used as controls.

The experiment demonstrated that LO-CD2b is reactive with a lysed PBMC supernatant of a molecular weight of 52 kDa (data riot shown).

Saturation test. Ten ml of heparinized peripheral blood was diluted in 25 ml of RPMI and the solution was centrifuged across a density gradient of LSM. The isolated PBMCs (7×106 cells/ml) were incubated for 30 minutes with 25 μl of naive baboon serum to saturate the Fc receptors. After 2 rinses, PBMCs were incubated with serial dilutions of LO-CD2b (from 80 μg/ml to 0.3 ng/ml) for 30 minutes. The LO-CD2b coating was revealed using a peroxidase-labeled mouse anti-rat IgG2b (MARG-2b). The different samples were analyzed by FC.

By FC, the mean fluorescence intensity increased from a concentration of 312 ng/ml until a saturation plateau beginning at 20000 ng/ml and over (FIG. 2).

Example 3

LO-CD2b Inhibits Mitogenic Stimulation of Baboon PBMCs

LO-CD2b inhibits a mitogenic stimulation even when added 3 days after the initiation of the culture.

Isolation of baboon PBMCs. Ten ml of heparinized blood were diluted in 25 ml RPMI and the PBMCs recovered after centrifugation across a density gradient on LSM. The isolated PBMCs were blended in enriched MLR medium. PBMCs were adjusted at 4×106 cells/ml and suspended in 100 μl of enriched medium. 4×10$^6$ cells/ml were plated in 96-well microtiter plates and either 20 μl PHA (80 μg/ml) or 20 μl ConA (25 μg/ml) was added. LO-CD2b was added at a concentration of 200 ng/ml 0, 24 hr and 48 hr after the beginning of the incubation. Another rat IgG2b of an Ig-secreting immunocytoma IR863 was used as control. Ninety six hours after the initiation of the mitogenic stimulation, the plates were incubated for 4 hours with tritiated thymidine (1 mCi/ml, Amersham Life Science, Belgium) and then harvested (Filtermate 196, Packard) and counted (Top count, microplate scintillator counter, Packard).

At day 0, an inhibition of the baboon PBMCs proliferation induced by PHA (72.8±12.1%) and by ConA (71.0+8.4%) was observed in presence of 200 ng/ml LO-CD2b mAb. The antibody was still able to partially inhibit the response to both mitogens even if added 1 or. 2 days after the culture initiation. In fact, when LO-CD2b was added to the culture at day 1 and 2 after initiation, the inhibition of the proliferation after PHA stimulation reached 56±8.5% and 38.5±9.8% respectively. Similarly, the inhibition of proliferation after ConA stimulation was 29.3±7.5% and 15.7+ 11.5%, when added on day 1 and 2 respectively (FIG. 3A). LO-CD2b had a similar inhibitor effect on PHA stimulated human PBMC (FIG. 3B). In the presence of human PBMCs, the inhibition by PHA was 62.1 at day. 0, 48% at day 1 and 18% at day 2.

Example 4

LO-CD2b Inhibits Allogeneic Stimulation

Isolation of baboon and human PBMCs. Ten ml of heparinized blood were diluted in 25 ml RPMI and the PBMCs recovered after centrifugation across a density gradient on LSM. The isolated PBMCs were blended in enriched MLR medium. PBMCs were adjusted at $4\times10^6$ cells/ml and suspended in 100 µl of enriched medium.

Mixed lymphocyte reaction. $1\times10^6$ baboon or human responder cells suspended in 100 µl medium were incubated with similar number of irradiated (25 Gy) mismatched baboon or human stimulator cells. The culture was carried out in triplicate in 96 U-Well microtiter plates (Falcon, Nunc Brand products, Denmark). The plates were incubated 6 days at 37° C., 5% $CO_2$. After this period, the cells were pulsed with 25 µCi/well of tritiated thymidine for 5 hr, harvested and counted. All results are expressed in raw count (cpm) as the mean of three wells. The LO-CD2b was added either at different concentrations (10 µg/ml to 610 pg/ml) from the beginning of the culture or at a constant concentration (5 or 0.5 µg/ml) on different days (day 0 to day 4) after the initiation of the culture. A rat anti-DNP antibody of IgG2b isotype (LO-DNPI 1) was used as negative control at the same concentration and the same time. The percentage of MLR inhibition was obtained by the ratio of cpm from the wells with LO-CD2b to the cpm of the wells with the medium alone.

Dose effects. When LO-CD2b was added at the initiation of the baboon allogeneic, a dose as low that 78.1 ng/ml was able to inhibit the proliferative response (77.9±13.7%). Low doses such as 4.8 and 9.7 ng/ml still inhibited 50% of the MLR. Even a very low dose (1.2 ng/ml LO-CD2b) could inhibit the proliferation up to 22.9±14.1% (FIG. 4A). Between a concentration of 312 and 10000 ng/ml, we observed a stable and major inhibition of MLR (96.4±1.1%). The same effect was observed in allogeneic human MLR but with a lower degree of inhibition. Even at 1.2 ng/ml, the inhibition was 15% (FIG. 4A). In comparison, no inhibition was obtained with a rat IgG2b isotype control (data not shown).

Kinetic effects. Similarly to the inhibition obtained with mitogens, LO-CD2b was able to block an allogeneic stimulation even when added to human and baboon PBMCs culture 1, 2, 3 and 4 days after initiation. Even three days after initiation, 5000 ng/ml LO-CD2b mAb was able to inhibit the allogeneic MLR up, to 24.8 and 27.1% respectively (FIG. 4B).

When the cells were incubated with rat IgG2b isotype control (LO-DNP11) there was no inhibition. Similar results were obtained with both human and baboon PBMC (FIG. 4B).

Secondary MLR. $2\times10^5$ responder baboon lymphocytes were cultured with a similar amount of irradiated (25 Gy) lymphocytes from an histoincompatible baboon in presence of LO-CD2b (100 ng/ml) for a six days primary culture. A rat anti-DNP antibody of IgG2b isotype (LO-DNP11) was used as negative control. After 6 days, the cells were harvested, washed and maintained in culture during 3 additional days at 37° C. without antibody. After 3 days, the cells were re-stimulated by the same irradiated stimulator cells or third party cells (at the concentration of $2\times10^5$ cells/100 µl) Similarly pre-cultured cells were stimulated with ConA (0.4/µg/ml) in order to compare a specific allogeneic and mitogenic stimulation. Three days after the initiation of this secondary culture, the plates were pulsed with $^3$ H thymidine and harvested as described above.

After primary MLR, baboon responder PBMCs which have been previously incubated with LO-CD2b were unable to respond to a second stimulation with the same allogeneic stimulator cells whereas these cells responded to ConA. These results suggest induction of a specific hyporesponsiveness through TCR interaction (data not shown).

It can elicit a strong inhibition of the allogeneic MLR at subsaturating nanogram concentrations, even when added as late as four days after the initiation of the culture. These observations suggest that LO-CD2b not only inhibits the activation of CD2$^+$ cells but also down-regulates activated T cells. These results differentiate this mAb from other anti-T cell mAb such as OKT3 which eliminates but also activates T cells (Sgro, C. 1995. *Toxicology,*105:23.) or such as OKT11 which does not activate and does not inhibit T cells (Latinne et al. 1996. *Int. Immunol.* 8: 1113; Schwarz et al. 1995. *J. Immunol.* 154:5813) or the blocking and non-activating anti-Tac mAb (Depper et al. 1983. *J. Immunol.* 131: 690; Hakimi et al. 1997, Development of Zenapax®; a humanized anti-tac antibody, in *Antibody Therapeutic,* eds Harris and Adair, Boca Raton, Fla.: CRC Press. One of the most interesting characteristics of LO-CD2b is its ability to block both human and nonhuman primate allogeneic proliferative responses, thereby rendering it an important experimental tool which could provide relevant results at both the pre-clinical and clinical levels. In addition, LO-CD2b seems to have similar in vitro and in vivo characteristics as LO-CD2a/BTI-322®, which is in clinical trials for organ transplantation. In fact, LO-CD2a, reverses renal rejection episodes (Mourad et al. 1997. *Transplantation Proc.* 29: 2353) decreases the incidence rejection when used in prophylaxis (Latinne et al. 1996. *Int Immunol.* 8: 1113) and is able to control control cortico-steroid resistant graft versus host disease (Mourad et al. 1997. *Tranasplantation Proc.* 29: 2353; Latinne et al. 1996. *Int Immunol.* 8: 1113). LO-CD2a has been humanized (MEDI-507, MedImmune Gaithersburg, MD) and approved for use in clinical trials. LO-CD2b has the potential to become the experimental counterpart of LO-CD2a.

Example 5

LO-CD2b Inhibits Cytokine Release Following Mitogen Stimulation

Baboon PBMCs ($1.5\times10^6$ ml) were incubated at 37° C. with 5% $CO_2$ in enriched MLR medium for 12 hr, 24 hr and 48 hr in presence of either LO-CD2b at different concentrations (1 µg/ml, 0.5 µg/ml, 250 ng/ml and 125 ng/ml), rat immunocytoma IR863 (1 µg/ml), rat lgG2b isotype, 20 µl LPS (20 ng/ml), 20 µl PHA (80 ng/ml) or 20 µl ConA (25 µg/ml). After stimulation, the supernatants were collected and stored at −80° C. until assayed for production of cytokines by using specific ELISA kits (Predicta, Genzyme, Cambridge, USA)

The incubation of baboon PBMCs with different concentrations of LO-CD2b produced very low levels of TNF-α (<17.2 pg/ml) (FIG. 5A), IFN- (<126 pg/ml) (FIG. 5B) and IL-2 (<21.9 pg/ml) (FIG. 5C) after either 12, 24 or 48 hours. The production of cytokines was significantly higher when baboon PBMCs were stimulated using the mitogens PHA, ConA and LPS i.e. positive control. Conversely, as a negative control, lymphocytes were incubated alone or with a rat IgG2b isotype control (IR863).

Example 6

In Vivo Allogeneic Studies Using LO-CD2b
Methods

Animals. Outbred baboons, male and female (Papio hamadryas), weighing 10–15 kg were used in this study. The animals were maintained in a restricted-access facility. All animals were negative for hepatitis and Simian T lymphotropic virus (STLV). The baboons received U.A R. monkey 107 food ad libitum. The first criteria for selecting pairs of recipient and donor was the compatibility of the ABO blood groups. Then, in order to select histoincompatible animals, one way MLR was carried out and baboons that mounted a strong proliferative response (stimulation index index at least 10) were selected. In order to assess the presence of anti-baboon antibodies, a cross-match was performed. The animals received no blood transfusion or medication before treatment or transplantation.

Transplantation. All animals were anesthetized with tiletamine/zolazepam (Zoletil® 100) (6 mg/kg) for induction and enflurane (Ethrane® 0.8%)/nitrous oxide (0.2 l/min) for mairitenance. An endotracheal tube was used for continuous delivery of oxygen (0.5 l/min) during anesthesia. Buprenorphine (Temgesic®) was given for 5 postoperative days with parenteral antibiotics (Clamoxyl®). In the donor, the left kidney was harvested and a Dacron® prosthesis was sutured on the aorta in order to maintain the right kidney and the baboon alive for future immunological testing. In the recipient of an allogeneic renal transplant, a bilateral nephrectomy was performed through a midline laparotomy. The kidney allograft was transplanted end-to-side to the aorta and vena cava in the iliac fossa by a running suture (Prolene® 6/0, Ethicon®, Johnson and Johnson, USA). The ureter was implanted into the bladder through a neocystostomy. A permanent catheter was positioned in the jugular vein and a jacket system (LOMIR® Canada) adapted in order to monitor daily several blood testing such as plasma creatinine, hematocrit, lymphocyte counts without the need for anesthesia. When transplant rejection occurred, as evidenced by persistent elevated creatinine (>6.0 mg/dl), the animal was euthanized.

Experimental groups. Three groups of baboons were used in this experimental protocol (Table 1). In Group 1, the baboons received single injection of LO-CD2b mAb at different doses or multiple LO-CD2b injections at a similar dose but during different time of administration (3 or 12 days). LO-CD2b, in warm saline, was injected over one hour through the jugular line. These animals did not undergo a renal transplant. In Group 2, two animals received LO-CD2b for twelve consecutive days as well as a kidney renal allograft. Group 3 consisted of a non-imunosuppressed baboon, serving as a control of allograft survival, a second animal (#33) which received total body irradiation (2×1.5 Gy) and a third animal (#44) which underwent total body irradiation (2×1.5 Gy) and a three day regimen of LO-CD2b at 2 mg/kg/day and finally, a fourth animal which received three doses (3×50 mg/kg) of ATG (anti-thymocyte globulins, Upjohn, Kalamazoo, Mich.).

Hematology analysis. Blood samples were taken daily and analyzed with a blood counter (MS9 vet, Melet Schloesing lab, France). The total number of red blood cells, platelets and leucocytes were obtained daily for all animals during at least two weeks.

Peripheral and lymph node lymphocyte monitoring. The phenotype of peripheral lymphocyte subpopulations was monitored by FC analysis using a panel of labeled (fluorescein or rhodamine conjugated) mAbs including: anti-CD2 marker (T11; Coulter® and Leu-5b; Becton Dickinson), anti-CD4 (T4; Coulter, anti-CD20 (B1; Coulter) anti-CD3 (BioSource), anti-CD8 (Leu-2a; Becton Dickinson). MARG-2b (Mouse Anti-Rat IgG2.b) and IR-863 (rat myeloma protein of IgG3b isotype served as controls. Blood samples were taken at days 0, 3, 7, 10, 17 and 22 after treatment. The relative numbers of CD cell subpopulations were determined in each animal. The lymphocyte phenotype was similarly studied in the lymph node on days 0, 7 and 10. The lymph nodes were excised from the inguinal area. In order to estimate the T cell depletion the lymph node was. crushed after excision and the total cell count of lymphocytes assessed per gram of tissue. Cells were analyzed on a Becton Dickinson FACS analyzer and the mean fluorescence intensity assessed for each marker.

Anti-rat immunoglobulin response. After LO-CD2b treatment, plasma samples were assayed for the presence of monkey antibody to rat IgG2b by using an ELISA assay. Nitrocellulose (0.4 $\mu$m)-coated 96 microtiter well plates were incubated overnight with the rat IgG2b (LO-CD2b) mAb (10 $\mu$g/ml, 4° C.) in borate buffer (pH 9.5). Plates were washed 3 times, incubated (1 hour at 37° C.) with skimmed 5% milk in PBS and washed 3 times in PBS 0.1% TWEEN. Microtiter plates were incubated with serial dilutions (1/200 . . . ) of monkey serum, and baboon Ig were detected by peroxidase-labeled rat antihuman IgM (LO-HM22) or IgG (LO-HG22). The plates were developed using orthophenyldiamine (OPD, Sigma), 0.03% $H_2O_2$ (MERCK) in citrate buffer (pH 5.5) solution. Optical density was measured at 492 nm using an optical reader (Labsystems, Multiskan RC, Finland).

LO-CD2b concentration. In order to assess the LO-CD2b concentration in the serum of treated monkeys, a sandwich enzyme-linked immunoadsorbent assay (ELISA) technique was used as previously described. Briefly, the microtiter plates were coated overnight at 5° C. with mouse anti-rat IgG2b, after saturation of nonspecific antigenic sites with skimmed milk. The plates were then incubated with serial dilutions of baboon serum. The rat Ig was detected by peroxidase-labeled mouse anti-rat kappa light chain mAb (MARK-1) and OPD development (Sigma). Purified rat IgG2b was used as standard. In order to evaluate the Ig serum concentration in treated monkeys, serial dilutions (1 $\mu$g/ml). of purified LO-CD2b was used, and the serum Ig concentration was measured after LOGIT transformation of standard and test serum serial dilution curves.

Immunohistology. Biopsies of inguinal lymph nodes were taken on days 0, 7 and 10 after the start of LO-CD2b treatment or TBI, ATG treatment. The tissue was immediately placed in Bouin fixative, and then cut into sections and stained with hematoxylin. and eosine for histology. For immunohistological studies, the lymph node tissue was washed in toluol, propanol and ammoniacal acid, and the slides suspended in 0.3% $H_2O_2$. After water and 50 mM Tris HCl, pH 7.5 washes, the non specific antigenic sites were saturated with NGS (normal goat serum) 1/10 and BSA(1%) for 30 minutes. In order to observe T, B and macrophage cells, the tissue was incubated with rabbit anti-human CD3 (Dako), Clonab MB2 (all B cells, Biotest). and mouse anti-human CD68 (Dako) overnight at 4° C. after addition of Tris-NGS 1%. After washing in 0.05% triton buffer, the slides were coated 30 minutes with biotin conjugated secondary antibodies (anti-mouse or anti-rabbit (Boehringer in Tris-NGS 1% and skimmed milk 5%). Peroxidase labeled streptavidin was deposited during 30 minutes after washing and the peroxidase-labeled slides were revealed by diaminobenzidine (DAB), 30% hydrogen peroxide in water and in Tris-NGS 1% buffer. The reaction was stopped with water. The slides were then placed in hemalun, propanol, toluol and xylene for one second each.

Indium-111-Ozine labeled leukocyte scintillography. Forty milliliters PBMCs were isolated from heparinized blood by density gradient centrifugation on LSM. Isolated PBMCs were suspended in physiological water and incubated 15 minutes with 780 µCi (28,860 MBq) of $^{111}$Indium-Oxine (Amersham Healthcare) at 37° C. The complex is neutral and lipid-soluble and penetrates the cell membrane of the lymphocytes. Within the cell, the indium attaches to cytoplasmic components. The labeled cells were washed with 50% autologous plasma in ACD buffer and the free indium released by the cells. The pellet was resuspended in 4 ml autologous plasma for injection. This suspension was injected in a male baboon of 40 kg (#32). A blood sample was taken every 1–5 minutes during a 70 minute experiment. Thoracic and abdominal were performed simultaneously. The scans were performed with a γ-camera coupled to a computer with a medium energy collimator. LO-CD2b was injected at 2.5 mg/kg 20 minutes after the injection of the $^{111}$Indium-labeled leukocytes.

Assessment of the classical and alternative pathway of complement (CH50 and AE50). Serum samples were collected before LO-CD2b injection, a half hour, and one hour after administration and frozen at −80° C.

Classical pathway. 50 µl of a 1:10 dilution of each serum sample was prepared in ice-cold GVB++ buffer. 25 µl of a suspension of sheep erythrocytes sensitized with rabbit anti-sheep erthryocyte antibodies were added to each serum dilution sample to produce cellular antigen-antibody complexes. These complexes were incubated 60 min at 37° C. 1.2 ml of 0.15M NaCl was added to each tube to stop the reaction and after centrifugation during 5 min at 1250 g, the supernatants were analyzed on a OD 412 reader. CH50 U was defined as the dilution of serum which lyses 50% of the cells in the assay.

Alternative pathway. 100 µl of serial 1.5 fold dilutions of each serum sample in GVB/MgEDTA buffer were added with 100 µl of rabbit erythrocytes during 60 min at 37° C. 1.2 ml of 0.15 M NaCl was added to each tube. The supernatant of each dilution was examined after 5 minutes of 1250 g centrifugation Results Peripheral lymphocyte depletion. The count of peripheral blood lymphocytes after different treatments is presented in Table 2. Independently of the LO-CD2b dose used, one hour after a single injection, 82.4±15.1% of the peripheral lymphocytes disappeared from the peripheral blood (FIG. 6A). After 24 hours, however, the recovery of the peripheral lymphocytes was dependent on the treatment used (Table 2): after a single injection, the lymphocytes reappeared in the peripheral blood two to three days after injection; after a three day course, the lymphocyte reappearance in the periphery occurred one week after the end of the treatment and after a twelve day course, the peripheral blood depletion was maintained for at least two weeks. Animal #23, in fact, demonstrated a significant peripheral depletion up to 45 days after the end of the LO-CD2b regimen. No obvious toxicity after single or iterative LO-CD2b administrations was evidenced in any baboon even at high doses such as 2 mg/kg.

In comparison to LO-CD2b treatment, a total body irradiation of 2×1.5 Gy produced a slower but more profound depletion of the circulating peripheral T cells. Between 5 and 20 days after such an irradiation, only 25% of peripheral lymphocytes survived and the pre-irradiation level was achieved only after three weeks (FIG. 7). The addition of a three-day regimen of LO-CD2b to a similar TBI seemed to produce even a stronger depletion and the animal died on post-irradiation day 16. In contrast, a three day regimen of ATG (50 mg/kg/day) did not provide a significant peripheral T cell depletion and 6 days after the third ATG injection the level of circulating lymphocytes rebounded above the pre-treatment value. During the treatment, the peripheral depletion never exceeded 50%.

Phenotype of peripheral lymphocytes after LO-CD2b treatment. As illustrated in Table 3, the percentage of $CD2^+$, $CD20^+$ and $CD16^+/CD2^+$ cells are shown in one representative LO-CD2b treated (#42) and one untreated animal (#15). For all treated baboons, an average reduction of 92.9±5.1% (81.3±7.3 to 5.6±3.9) of $CD2^+$ cells was observed between day 0 and day 3. After 20 days, the percentage of $CD2^+$ cells was 36.3±16.8%. In contrast, the-percentage of B lymphocytes ($CD20^+$ cells) increased from 19.9±13.2% to 45.0+21.7% during the same time period. The $CD2^+$ NK cells were also affected by the LO-CD2b treatment, as the percentage of $CD16^+/CD2^+$ cells dropped from 11.3±2.5% to 0.9±0.3% (a reduction of 92.0%) in the peripheral blood. These $CD16^+/CD2^+$ cells returned at the pre-treatment level after 20 days.

By mean fluorescence intensity, the course of $CD2^+$, $CD20^+$ and $CD16^+/CD2^+$ peripheral cells was comparable (Table 3).

Lymph Mode Depletion: Absolute Count, Phenotype, and Immunohistology

Absolute number of cells in lymph node (Table 4). In LO-CD2b treated baboons, the absolute number of cells per milligram of tissue decreased between D0 and D7 when a dose of 1 or 2 mg/kg was used. The pre-treatment level was however restored after the LO-CD2b injection. In comparison, one animal underwent a three day treatment with rabbit anti-T cell globulins (3×50 mg), but no lymph node depletion was evidenced in this case. A total body irradiation (3 Gy) in contrast clearly provided a lymph node depletion which seems more durable (over day 10) and the addition of LO-CD2b to the TBI was even more efficient in terms of lymph node depletion (FIG. 8)

Phenotype. As illustrated in Table 3 for representative animal #42, both percentage and mean fluorescence intensity decreased for $CD2^+$ cells between D0 and D7 in the lymph node, but ten days after the initiation of the treatment, the $CD2^+$ cells returned to pre-treatment values. In contrast, the relative count of B lymphocytes (and the MFI) increased between D0 and D7, to eventually return to the pre-treatment level ten days after treatment.

Lymph node immunohistology. Between D0 and D10, we observed a partial depletion of T cells in the deep cortical area. On immunohistology, the $CD3^+$ cells were depleted at D7 and D10 in comparison with D0. In contrast, the B cell population seemed more prevalent as assessed by MB2 staining and more follicles were seen at D7 and at D10. In comparison, the baboon receiving :a total body irradiation of 3 Gy showed a T cell depletion in inguinal lymph node as assessed by CD3 staining on day 7 and 10 after treatment (FIG. 8).

Free and coated LO-CD2b levels. The free LO-CD2b concentration in the sera of treated baboons was never high and did not exceed 2.5 µg/ml during LO-CD2b treatment. Such a serum concentration was however reached only after high dose injections (2 mg/kg). Despite frequent administrations (twelve days), LO-CD2b was never found in excess after 5 or 10 days. In order to observe the coated LO-CD2b mAb, PBMCs were incubated with fluoresceinated mouse anti-rat IgG2b mAb and the percentage of positive cells assessed by FC. From D0 up to D10 the percentage of coated cells varied between 2% and 44.2%. In the lymph nodes, LO-CD2b coated T cells were not detected.

Mechanism of LO-CD2b T cell depletion. Immunization against LO-CD2b. Anti-rat antibodies were already detected 8 days after the first injection in all animals and became stronger after 10 days, whereas the sera prior to the treatment were uniformly negative (data not shown).

Indium scintillography. As illustrated in FIG. 9, the $^{111}$Indium activity in the whole blood significantly decreased and there was no concomitant increase in the serum. This blood activity decrease was, however, correlated with a significant increase of the radioactivity in the liver and the spleen, thereby suggesting a sequestration of the PBMCs in the reticulo-endothelial system of these two organs.

Complement dosage. The assessment of both classical and alternate pathways of the complement system did not vary after injection of LO-CD2b. This result suggests that the disappearance of the $CD2^+$ cells from the peripheral blood was not driven by a complement dependent mechanism (Table 5).

Renal graft survival and histology. Without treatment, animal #15 (control) died on postoperative day 10 in uremia. In comparison, animal #23, which received a twelve-day regimen of LO-CD2b (0.35 mg/kg) rejected the renal allograft and died in uremia on postoperative day 15. A second baboon (#25) died on postoperative day 20. during anesthesia (for a surgical biopsy) whereas the renal function was normal (creatinine 1 mg/dl) (FIG. 10).

LO-CD2b elicits in vivo a strong depletion of $CD2^+$ cells in the peripheral blood. Thirty minutes after a single dose injection of LO-CD2b, the absolute count of lymphocytes dropped by more than 80%. Among the remaining cells in the PBL, there were mainly $CD20^+$ cells, very few $CD2^+/CD4^+$ or $CD2^+/CD8^+$ T cells and a small number of NK $CD2^-$ cells. This peripheral depletion was therefore important on both circulating T and NK $CD2^+$ cells. The depletion was, however, reversible several days after the treatment and directly dependent of the dose and duration used. After a single dose, the peripheral lymphocytes reappeared two or three days after in the peripheral blood whereas a three-day regimen resulted in an almost one-week long depletion. A twelve-day course of low LO-CD2b doses (0.35 mg/kg) produced a long-lasting T cell depletion lasting 3-4 weeks. In vivo, LO-CD2b appeared safe and seemed to deplete without activating lymphocytes or producing cytokine release. In vitro, there was in fact no cytokine release as assessed by ELISA. No side effects were evidenced after any dose or duration time period in vivo. The peripheral T cell depletion obtained by LO-CD2b could be the result of several mechanisms: (i) either by a complement dependent way or (ii) by ADCC or (iii) by opsonization and destruction of the T cells in the reticuloendothelial system. We found that activation of the classic or alternate pathway of complement was not involved in our experiments. As LO-CD2b also depleted in vivo a large percentage of NK $CD2^+$ cells it seems unlikely that ADCC is involved. The third possibility, namely opsonization seems to be involved as evidenced by the Indium scanning data. After LO-CD2b treatment, the concentration of Indium did not increase in the serum but significantly rose in the spleen and especially in the liver. The ligation of the FcR by the CH2 domain of the LO-CD2b antibody could result in opsonization and sequestration of LO-CD2b coated cells by the reticuloendothelial system, which is particularly important in the liver and spleen. Coated T cells would be subsequently destroyed by macrophage phagocytosis or by other $FcRIII^+$ cells (Majeau et al. 1994. *J.Immunol.* 152: 2753; Wee et al. 1989. *Transplantation*, 48: 1012).

The use of 3 Gy TBI to effect peripheral T cell depletion and which is used in protocols for inducing mixed chimerism (Kawai et al. 1995. *Transplantation*, 59: 256) produced, in comparison, progressive but more profound and long-lasting T cell depletion than LO-CD2b treatment alone. Similar results were obtained with the combination of TBI and LO-CD2b. In contrast, ATG which has been used in several protocols for inducing tolerance to primarily vascularized allografts in primates (Carver et al. 1991. *Transplantation. Proc.* 23: 480; Thomas et al. 1989. *Transplantation*, 47: 209), did not provided a strong and long-lasting T cell depletion.

LO-CD2b elicits a strong depletion in the periphery, and a moderate depletion in the lymph nodes at a dose higher than 1 mg/kg and during three consecutive days. After single or three day injections, there was a moderate depletion of T cells in the lymph nodes as assessed by the absolute number of lymphocytes per gram of tissue, especially between D0 and D7. By flow cytometry, LO-CD2b effected a reduction in the percentage and in the mean fluorescence intensity of the $CD2^+$ cell population (also $CD4^+$ and $CD8^+$) between D0 and D7. These results were confirmed by immunostaining experiments. This lymph node T cell depletion was however less important than after a sub-lethal dose (3 Gy) of total body irradiation and than the lymph node depletion obtained with the combination of both agent. In contrast, ATG had no depleting effect on lymph nodes.

Peripheral depletion is not absolutely required for obtaining prolongation of primarily vascularized allografts. OKT4 (anti-CD4 mAb) in fact, prolonged allograft survival in primates without $CD4^+$ T cells depletion (Cosimi et al. 1990. *Surgery*,108: 406. On the other hand, several authors showed that when the number of peripheral blood T lymphocytes was reduced to below 10%, the incidence of rejection was reduced in treated renal allograft patients (Knechtle et al. 1997. *Transplantation*, 63:1; Thomas et al. 1997. *Transplantation*, 64: 124; Cosimi et al. 1976. *Surgery*, 80: 155). In order to induce mixed chimerism, however, a peripheral T cell depletion seems important at least transiently and T cell depletion at the level of the lymph node and thymus is also necessary from reports using rodents (Shoskes. 1996. *World J Urol.* 14: 218; Krieger et al. 1996. *Transplantation*, 62: 1285). Transient but profound depletion of the recipient T cell population seems to favor the establishment of tolerance. There is no such immunosuppressive drug in large animals, thereby rendering mandatory the use of sublethal total body irradiation as an important tool for tolerance induction protocols. The replacement of total body irradiation by an easily controllable agent would of course be important to apply such tolerance protocols in humans, especially in children. Recently, the production of FN18-CRM9, composed of an anti-CD3 mAb and a binding site of diphtheria toxin, may be the first step in this direction, since this agent causes a strong and transient T cell depletion in the peripheral blood (2–4 weeks), but also in the lymph nodes. This agent has shown remarkable success in primate renal allografts (Knechtle et al. 1997. *Transplantation*, 63:1) and clearly demonstrated that mixed chimerism and tolerance could be obtained in primate without requiring total body irradiation (Thomas et al. 1997. *Transplantation*, 64: 124). The use of such immunosuppressive agent in humans will however need the evidence of its safety and among the main undesirable effect, the long-lasting peripheral T cell depletion could prohibit its use in clinical trials. The preexistence of immunization response against toxin diphtheria could also reduce the efficiency of this agent.

The lymph node depletion is pertinent for tolerance strategies and peripheral T cell depletion must persist for at least one or two weeks after completion of T cells (Rao et al. 1991. *Transplantation*, 52:691).

Relatively little data in primates and in human have been published on the influence of monoclonal anti-lymphocyte anti-bodies on lymphocytes in lymph nodes. The use of a humanized IgG1 anti-CD4 mAb results in a lower level of depletion in the lymph node than in the peripheral blood whereas using the IgG4 isotype form of the humanized anti-CD4 mAb resulted in only a coating of CD4+ cells and no depletion (Mourad et al. 1997. *Transplantation Proc.* 29: 2353; Cosimi et al. 1990. *Surgery,*108: 406).

Treatment with LO-CD2b as a single agent resulted in a modest but significant prolongation of allograft survival times. Whereas untreated baboon died in uremia within ten days after transplantation, the LO-CD2b regimen increased the graft survival up to. 15 and 20 days. A second animal died with a normal renal function during anesthesia for surgical biopsy.

In conclusion, LO-CD2b is a non-activating anti-CD2 mAb which inhibits allogeneic response and might induce antigen-specific unresponsiveness. In vivo, LO-CD2b produced a strong depletion of CD2 + cells (T cells and NK cells) in the peripheral blood and a moderate depletion of CD2+ T cells in lymph nodes with no apparent side effects. The depletion is however generally reversible within the days after the end of the treatment and therefore monitorable. The mechanism of action of LO-CD2b could be either ADCC-dependent and or by opsonization in the reticuloendothelial system. LO-CD2b injections significantly prolong renal allograft survival in baboons.

These findings suggest that LO-CD2b is a potent immunosuppressive drug which should be tested in tolerance protocols without total body irradiation. In combination with donor bone marrow infusion, LO-CD2b could be a good candidate to induce mixed chimerism in primate experiments. In addition, the fact that LO-CD2b seems to have the same characteristics than LO-CD2a (BTI-322®/MED507) which already demonstrated efficacy in human clinical trials, renders LO-CD2b as a very important tool to study in pre-clinical models, protocol of tolerance induction.

Example 7

In Vitro and In Vivo Effects of LO-CD2b on Pig to Baboon Xenogeneic Cellular (T and NK Cells) Immune Responses Hyperacute vascular rejection (HAVR) represents the primary barrier to xenotransplantation between discordant species. Recent advances in the prevention and the understanding of HAVR however, evoked questions about the importance of cellular immunity in baboon and human anti-pig xenogeneic immune response (Fryer, et al., *Transplant Immunnol.,* Vol 2, pgs. 87–93 (1994)). In fact, the xenogeneic cellular response as well as the acute vascular rejection represent now the main hurdle to primarily vascularized xenograft from pig to primates and probably to humans. The exact role of several immune cellular actors needs to be studied in vivo in discordant pig to baboon models i.e., macrophages, monocytes, granulocytes, and NK cells, as well as their role in combination with preformed antibodies (ADCC). Several groups have shown that recognition of xenogeneic targets by human T cells occurs: human anti-porcine mixed lymphocyte reactions (MLR) are comparable to allogeneic responses suggesting that CD4+ T cells recognize and react to porcine SLA Class II molecules. Swine MHC-restricted human cytolytic T lymphocytes can recognize SLA class I on porcine targets and induce a CD8+ T cell-mediated cytotoxicity. In addition to T cells, NK cells have been suggested to have an early and predominant role in cell-mediated xenogeneic cytotoxicity. Macrophages were rather considered as markers for tissue injury than the cause leading to the graft damage.

In the present example, the ability of LO-CD2b to inhibit in vitro a xenogeneic immune response and in vivo to eliminate the circulating NK CD2+ and T cells in the peripheral blood were evaluated. The results clearly showed that LO-CD2b produced in vitro a strong inhibition of the cellular xenogeneic immune response and in vivo, a rapid and severe depletion of peripheral CD2+/CD16+ cells thereby suggesting that this mAb represents a new interesting tool in the treatment of cellular xenogeneic rejection in both baboons and humans.

Materials and Methods

In vitro studies

Monoclonal antibodies and immunoglobulins. The LO-CD2b hybridoma. was produced as described above. The rat immunocytoma IR863 is an IgG2b used as antibody control.

Isolation of baboon peripheral blood mononuclear cell (PBMC) and lymphocytes (PBL). Three baboons were used as blood donor. Baboons #47 and #49 were naive animal whereas baboon #42 has been sensitized with 3 PAEC (130.000 cells/kg IV) injections at one week interval. Ten ml of heparinized blood were diluted in 25 ml RPMI and the PBMC recovered after centrifugation across a density gradient on LSM (LSM, International Medical, Brussels, Belgium). The isolated PBMC were blended in enriched MLR medium composed of AIM medium (confidential composition of Gibco including gentamycin (10 µg/ml), streptomycin (50 µg/ml), human albumin 0.1% (Gibco, Verviers, Belgium)) supplemented with 0.1 mM minimal essential medium (MEM, Gibco), 1 mM sodium pyruvate (Gibco), 20 M 2-mercaptoethanol, 2 mM L-glutamine (Gibco), 100 g/ml penicillin (Gibco), 100 g/ml streptomycin and 2% unrelated decomplemented (56° C., 0.5 h) baboon serum. PBMC were adjusted at $4 \times 10^6$ cells/ml and suspended in 100 l of medium for xeno MLR. For cytotoxic assays, PBMC obtained after Ficoll density centrifugation were resuspended overnight in medium 199 (Biowhittaker, Verviers, Belgium) including 20% foetal bovine serum (Gibco) and 100 g/ml penicillin, in a 25 cm² plastic tissue culture flask and PBL were purified from PBMC by removal of the adherent cells.

Isolation of porcine peripheral blood mononuclear cells. White Belgian landrace pigs from one local breeder served as source for pig PBMCs and were obtained from heparinized blood by Ficoll density gradient centrifugation using Lymphocyte Separation Medium. After harvesting the buffy coat, PBMCs were washed three times in RPMI buffer and resuspended for xeno MLR in the same medium and at $4 \times 10^6$ cells/ml.

Isolation of porcine aortic endothelial cells (PAECs). Porcine aortic endothelial cells were freshly harvested from pig aortic intrathoracical segments. The PAECs were obtained by scraping of the intimal surface of aortic segments. The cells were washed once in HBSS salt solution, resuspended in 5 ml of Medium 199 (Biowhittaker) supplemented with 20% foetal calf serum, 2 mM L-glutamine, 16.5 UI/ml heparin, 100 U/ml penicillin and 100 g/ml streptomycin. The cells were then seeded on a 50 ml tissue culture flask (Falcon, Becton Dickinson, Franklin Lakes, N.J., USA). After 24 hrs, the medium was renewed and changed twice. a week. When the cells were confluent, subcultures were obtained by trypsinization. Cells derived from passages 1–2 were used for cytotoxic assays.

Culture of K562 cells. Frozen NK-sensitive human erythroleukemic cell line K562 cells were thawed, washed three times in RPMI and suspended for culture in RPMI medium including 10% bovine foetal serum, 2 mM L-glutamine, 16.5 UI/ml heparin, 100 U/ml penicillin and 100 µg/ml streptomycin.

Flow cytometry. Phenotypic analysis of baboon PBL, before and after LO-CD2b/IR863 incubation, was carried out by flow cytometry (FC). After washing, PBL were suspended at 5×10⁵ cells per tube in PBS buffer and incubated for 1 hour at 4° C. with saturating concentrations of antibodies, directly conjugated either with fluorescein (FITC) or phycoerythrin (PE). FITC-anti-CD3 (Biosource), FITC-and PE-anti-CD2 (Coulter), PE-anti-CD8 (Becton Dickinson), PE-anti-CD4 (Coulter), FITC-anti-CD16 (Immunotech) and PE-anti-CD56 (Becton Dickinson) were used at the concentration recommended by the manufacturer. After three washes, the cells were analyzed for staining at both fluorescent wavelengths. LO-CD2b coated on CD2 cells was revealed by FITC mouse anti-rat IgG2b mAb (MARG2b).

In order to detect death cells, incubation with propidium iodide (5 μg/ml as final concentration) was carried out ten minutes prior to examination. Cell mortality was additionally evaluated by trypan blue vital coloration.

Xenogeneic mixed lymphocyte reaction. 1×10⁶ baboon PBMCs were suspended in 100 1 of AIM medium as responder cells and mixed with a similar number of irradiated (25Gy) porcine PBMCs as stimulator cells. The culture was carried out in triplicate in 96 U-well plates and incubated 6 days at 37° C., 5%CO₂. After 6 days, the cells were pulsed with 25 Ci/well of tritiated thymidine (1 mCi/ml, Amersham Life Science, Belgium) for 5 hrs, harvested and counted. All results are in raw count (cpm) as the mean of three wells. The LO-CD2b was added at 200 and 20 ng/ml from the beginning of the culture. A rat IgG2b isotype (IR863) was used as negative control at the same concentration. The percentage of MLR inhibition was obtained by the ratio of cpm from the wells with LO-CD2b to the cpm of the wells with the medium alone. Each experiment was done three times (PBMCs of the three baboons mixed each with the PBMC of three different pigs).

Cytotoxic assays. Fresh baboon PBL from naive baboon (#47 and #49) and from immunized baboon #42 were used as effector cells in standard $^{51}$Cr-release cytotoxicity assays with K562 cells or with PAEC as targets cells. K 562 cells were incubated with 100 Ci $^{51}$Chromium (Amersham Pharmacia Biotech)/2×10⁶ cells in 1.5 ml medium for 16 hrs at 37° C. Adherent PAEC were labeled in the flask with 150 Ci $^5$Cr/1 ml medium for the same time. After four washes, K562 and trypsinized PAEC target cells were added to triplicate samples of serial dilutions of effector cells in round-bottom 96-well plates at varying effector-to-target (E:T) ratios. All stages of these assays were set up in Medium 199 containing 20% of fetal calf serum. After incubation for 5 hrs at 37° C. in 5% CO₂, the plates were centrifuged (50 g) during 4 minutes. The supernatants were harvested and $^{51}$Cr-release. assessed by a gamma counter. Each experiment was done three times for each baboon. 200 ng/ml of LO-CD2b and of IR863 were incubated for 2 hours with PBL before the cytolytic assay. Baboon cells were then washed three times before re-suspension in medium 199.

ADCC. Baboon serum containing xenoreactive antibodies was obtained from a naive baboon (#47). Decomplementation by heat-inactivation was carried out at 56° C. for 30 minutes. Twenty microliters of this serum were added during 20 minutes to 200,000 cells/ml of PAEC. The cells were then washed three times before incubation with effector cells. Preformed antibodies concentrations were determined by ELISA and revealed a concentration of 32 g/ml of anti-galactosyl IgG and 212 q/ml of anti-galactosyl IgM. In order to assess ADCC phenomenon, the baboon serum was added to trypsinized PAEC during 30 minutes. The cells were then washed three times and used as target cells.

CML. In vitro stimulated baboon PBL were also used in similar experiment. 5×10⁵ fresh baboon PBMCs were added to a 25 cm² ml tissue flask cultured with confluent PAECs for 4 days in a final volume of 5 ml. After seeding and three washings, the baboon PBL were used as effectors in the same conditions than described above. Background cpm was taken as spontaneous release from target cells in medium alone, and maximum cpm as release by treatment of targets with 0.5% NP-40. Percentage of specific lysis was calculated as follows:

Specific lysis (%)=(cpm (experimental)−cpm(spontaneous)/cpm-(maximum)−cpm(spontaneous))×100.

In vivo studies

Animals. Outbred baboons, male and female (*Papio hamadryas*), weighing 10–12 kg were used in this study. The animals were maintained in a restricted-access facility. All animals were negative for hepatitis and Simian T lymphotropic virus (STLV). The baboons received U.A.R. monkey 107 food ad libitum. For in vivo experiments, animals were anesthetized with tiletamine/zolazepam (Zoletil$^R$ 100) (6 mg/kg) for induction and enflurane (Ethrane$^R$ 0.8%)/nitrous oxide (0.2 1/min) for maintenance. A permanent catheter was positioned in the jugular vein and a jacket system (LOMIR$^R$ Canada) adapted in order to inject the mAb and to withdraw blood and monitor daily blood parameters such as hematocrit, lymphocyte count, without the need for anaesthesia.

As shown in Table 2, five baboons received single or multiple injections of LO-CD2b mAb at different time (3 or 12 days) or different doses (0.25 mg/kg to 2.5 mg/kg). LO-CD2b was diluted in 50 ml saline and injected over one hour through the jugular vein.

Hematology analysis. Blood samples were taken daily and analyzed with a blood counter (MS9 vet, Melet Schoesing lab, France). The total number of red blood cells, platelets, leucocytes were obtained daily.

Peripheral lymphocyte monitoring. The phenotype of peripheral lymphocytes was monitored by FC analysis using a panel of labeled mAbs:rhodamine anti-CD2 marker (T11; Coulter), rhodamine anti-CD4 (Coulter), fluoresceinated anti-CD8 (Becton Dickinson) and fluoresceinated anti-CD16 (Immunotech). Blood samples were taken at days 0, 1, 7 and 14 after LO-CD2b injections. The relative percentage of CD2⁺, CD20⁺, CD2⁺/CD4⁺, CD2⁺/CD8⁺ and CD16⁺/CD2⁺ cells were determined for each animal. Cells were analyzed on a Becton Dickinson FACCS analyzer.

Results

In vitro results

Xeno MLR. Xenogeneic pig to baboon mixed lymphocyte reaction was inhibited at 91.3±5.6% after addition of 200 ng/ml of LO-CD2b and at 60.1±12.7% with 20 ng/ml of LO-CD2b (three samples from three different baboons were tested each against three different pigs). Representative results of baboon #49 are shown in FIG. 10. In comparison, no inhibition was observed in MLR with a rat IgG2b isotype control (IR 863). The inhibition of xenogeneic MLR by LO-CD2b was not the consequence of cell death: two hours incubation of baboon PBL with LO-CD2b did not cause death of mononuclear cells as demonstrated by propidium iodide staining at FC or by vital trypan blue coloration (Table 6). The number of cells coated with LO-CD2b was however, high as evidenced by FITC-mouse anti-rat IgG2b (MARG2b): 86.1% (PBMC) and 71.7% (PBL).

Baboon PBL anti-K562 cytotoxicity. As shown in FIG. 11, PBMC from naive baboons produced a spontaneous NK activity since cytotoxic lysis against K562 cells reached 59.5±10.6% at an E:T ratio. of 100/1. The K562 cytotoxicity was inhibited when the PBL were preincubated with 200 ng/ml of LO-CD2b at the same ratio (0.3±0.8%) whereas a similar lysis than without LO-CD2b was observed after incubation with the IgG2b isotype control (lysis of 54.5±5.6%). These results were repeated in three different experiments.

Direct Cytotoxicity of Baboon PBL to PAECs 1) in order to investigate spontaneous xenogeneic PBL cytolysis, freshly isolated baboon PBMCs were plated as effectors in presence of PAEC target cells. The anti-PAEC xenogeneic cytotoxicity of baboon PBMCs, expressed as a percentage of specific lysis at a 150 E:T ratio, reached an average of 41.0±14.0% as shown for the five. experiments illustrated in FIG. 12. This cytolytic activity was inhibited after addition of LO-CD2b.

2) In order to study the cytolitic anti-porcine response of baboon PBL primed by previous PAECs injections, PBLs from baboon #42 were incubated with PAECs and compared with PBLs from unprimed baboon. The lytic activity after previous priming was higher (59.3±7.3%) than the cytotoxicity obtained with PBL from unprimed animal #42 (33.3±5.0%). This lytic activity was however, also inhibited by LO-CD2b (−8.3±2.5 and −4.6±2.0% at the same 150 E:T ratio). (data not shown).

Direct anti-PARC cytotoxicity of baboon PBL in presence of xenoreactive natural antibodies. In order to assess ADCC phenomenon (FIG. 12), baboon serum (200 ng/ml) was incubated with PAECs. The direct anti-PAEC cytolysis observed was higher (66.4±5.5%) than the lysis found in serum free medium (41±14%), thereby suggesting that xenoreactive antibodies contributed to NK cell-mediated xenogeneic ADCC. This ADCC activity was however, blocked by LO-CD2b at a concentration of 200 ng/ml.

In vitro stimulation of baboon PBL leads to a significant increase in xenogeneic cytotoxicity. In order to study the effect of a previous xenogeneic stimulation on the cytotoxic response of baboon PBMC against PAEC, xenogeneic pig-baboon mixed cultures were set-up. After a 4 day incubation with PAECs, baboon PBLs demonstrated a higher cytotoxic activity to PAEC than unprimed baboon PBLs: 87.0±3.4% versus 28.6±7.0% at the same 150 E:T ratio (FIG. 13).

In Vivo Studies

In vivo $CD2^+/CD16^+$ cell depletion. After intravenous injections of LO-CD2b to various baboons at different doses and time (Table 7) a strong depletion of the $CD2^+$ and CD16+/CD2+ T cell population, (92.8±4.3%) was evidenced after 24 hours, independently of the LO-CD2b dose used. One hour after a single injection, 82.4±15.1% of the entire CD2+ population already disappeared from the peripheral blood. The recovery of the CD2+ population on day 7 was independent of the time and dose used. CD2+/CD16+ cells restored a level comparable with the pre-treatment value after 14 days (13.0±6.5% versus 11.9±6.0% respectively).

Discussion

In order to study the clinical situation of pig to human xenograft, the pig to baboon model is recognized as the best pre-clinical model. Although Acute Vascular Rejection (AVR) seems today the main obstacle to long-term success of xenograft survival, cellular rejection is also observed once hyperacute and acute vascular rejection are controlled. There is however few therapeutic agent which are specific for the pig to baboon model and particularly, specific anti-baboon T cell monoclonal antibodies do not exist. We showed in this study that LO-CD2b is an important monoclonal antibody in the pig to baboon xenogeneic model. In vitro, LO-CD2b inhibit a xenogeneic mixed lymphocyte reaction when baboon PBLs are stimulated by pig peripheral lymphocytes and prevent direct cytotoxicity of baboon PBLs against K562 cells and PAECS. In vivo, LO-CD2b elicits a strong depletion of baboon CD2+ peripheral lymphocytes as well as $CD2^+/CD16^+$ cells subpopulation.

As evidenced in xenogeneic MLR, baboon PBLs react strongly to PAEC. Yamada. et al., *J. Immunol.*, Vol. 155, pgs. 5248–5256 (1995), have previously shown that human PBLs are strongly stimulated by pig cells and that, anti-class II mAbs were able to partially block the proliferation thereby demonstrating that a part of human anti-pig xeno-response was directed toward porcine SLA class II Ags involving interaction with $CD4^+$ cells. Human T cells responded to xeno-MHC antigens in MLR at least as well as it did to allo-MHC antigens and appeared to share similar requirements for APC of either stimulator (direct pathway) or responder (indirect pathway) derivation. The partial blocking effect of anti-CD4 mAb and the little or no blocking effect of anti-CD8 mAbs suggested also the implication of other peripheral cells than T cells. It is known that when human T cells responded to xeno-MHC antigens in MLR, IL2 or IL12 cytokines which activate NK cells are produced and could explain the NK cytotoxicity in discordant xenogeneic models. The main advantage of LO-CD2b therefore resides in the possible inhibition of both T cells and $CD2^+$ NK cells. Since the inhibition obtained in MLR was not related to apoptosis or death of the cells, the mechanism of action of LO-CD2b should be related either to inactivation of the $CD2^+$ cells coated by the LO-CD2b mAb or an internalization of the CD2 molecule.

The spontaneous cytotoxic activity observed on PAEC could be attributed to NK cell cytotoxicity and we, in fact, evidenced a cytolitic NK activity against K562 target cells. This natural cytotoxic activity was however, stronger that the one reported by other authors (10%) using human fresh PBMC, purified human NK against PHA-stimulated porcine lymphoblasts or bone-marrow or aortic-derived endothelial cell lines. According to Itescu, et al., *Hum. Immunol,* Vol 59, pgs. 275–286 (1998), IL-2 augmented NK lysis involved interactions between the CD2 and CD49d molecules on baboon NK cells and their respective ligands on PAECs, since NK lysis was reduced either by using mAbs against CD2, CD49d, or porcine VCAM. These results showed that interactions between accessory molecule receptor-ligand pairs on primate NK cells, macrophages and porcine endothelium could be of critical importance in delayed xenograft rejection. In this study, it was shown that LO-CD2b inhibited the direct cytotoxicity of baboon PBLs against PAECs and K562 cells, probably by interacting with the CD2 molecule. The lytic activity enhanced by the presence of xeno-antibodies involving an ADCC mechanism, was also inhibited by LO-CD2b.

Primed and sensitized baboon PBLs and PBMCs demonstrated an increased cytotoxic activity. This cytotoxicity certainly involved cytotoxic T cell population concomitantly to NK cells. According to many authors, mAbs recognizing SLA class I antigens also blocked partially the cytotoxicity of human CTLs. These data suggest that human CTLs are heterogeneous regarding their molecular target specificity. In contrast other authors (Shishido, et al., *Transplantation,* Vol. 64, pgs. 340–346 (1998)) observed that the lysis of porcine targets by human $CD8^+$ CTLs was inhibited by mAb against SLA class I antigens and human CD8.

In vivo, LO-CD2b demonstrated a depleting effect on $CD2^+$ cells. In the baboon model, a rapid and marked loss of $CD2^+/CD16^{30}$ cells from the peripheral blood after LO-CD2b treatment was observed, and all T cell subsets were involved. Whether ADCC mechanisms are also important in vivo remains to be shown. The depletion of $CD2^+$ coated cells could result of several mechanisms including opsonization or destruction in the reticulo-endothelial system of the coated LO-CD2b cells by macrophages.

In conclusion, LO-CD2b seems very effective to inactivate the CD2+ population involved in the xenogeneic cellular immune response, including both NK and T cells. In vitro, the xeno MLR and the cytotoxic assays (against K562 and PAEC) were completely inhibited after incubation with LO-CD2b. In vivo, LO-CD2b produced a strong depletion of $CD2^+$ cells (NK and T cells) in the peripheral blood. These results suggest that LO-CD2b represents a new an interesting tool to inhibit the cellular component involved in the xenogeneic pig to baboon or human immune response.

The disclosures of all patents, publications (including published patent applications), and database accession numbers are incorporated herein by reference to the same extent as if each patent, publication, and database accession number were incorporated individually by reference.

It is to be understood, however, that the scope of the present invention is not to be limited to the specific embodiments described above. The invention may be practiced other than as particularly described and still be within the scope of the accompanying claims.

B. Course of MLR inhibition by LO-CD2b. The monoclonal antibody (5 μg/ml) was added from the initiation of the MLR (DO) to up to four days after the beginning of the MLR between two noncompatible monkeys or humans. Even when added two days after the initiation of the culture, LO-CD2b still was able to inhibit 50% of the MLR and 15% when added four days after the beginning of the culture.

Figure 1:
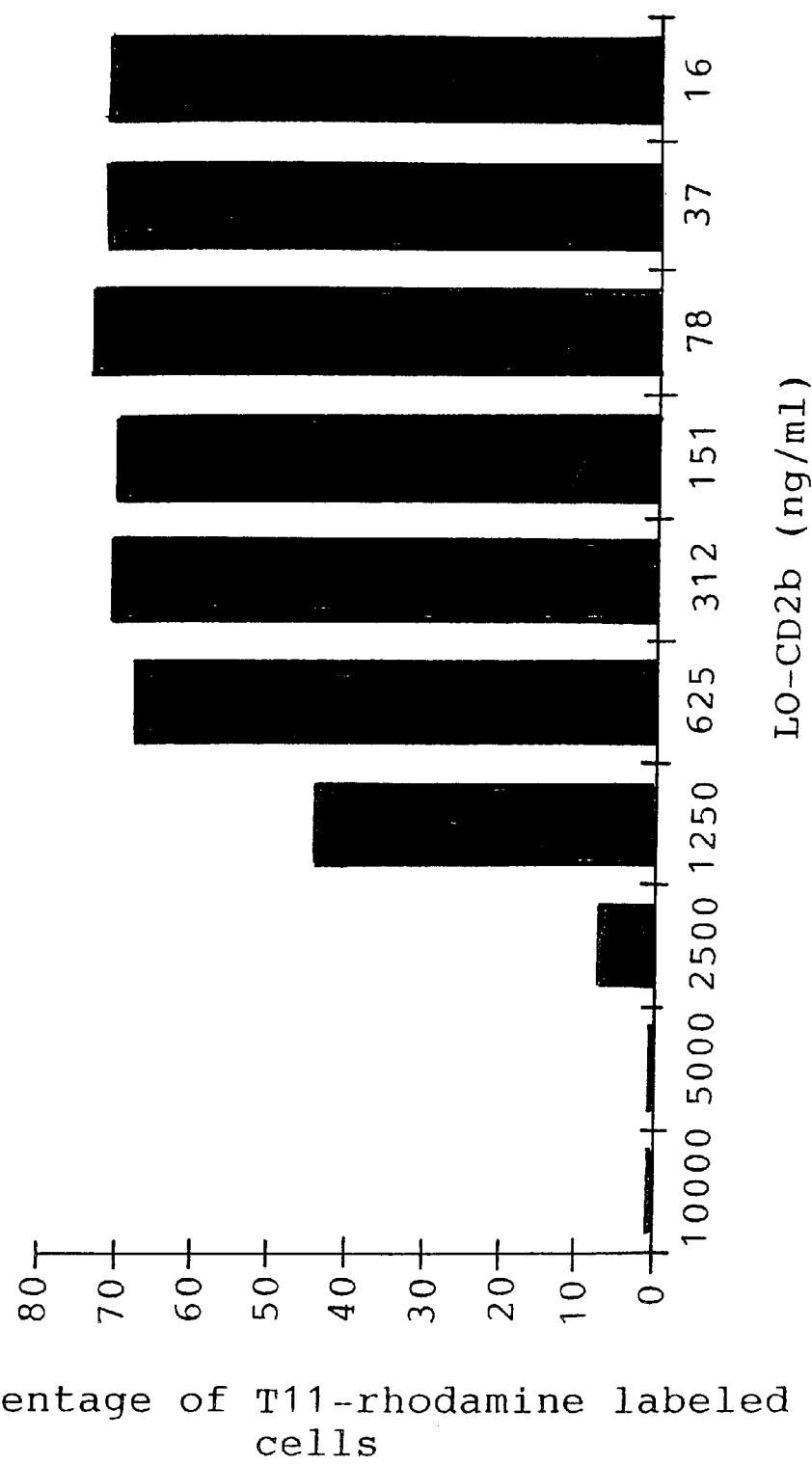
FIG. 1. Serial dilution of LO-CD2b (from 10000 ng/ml to 18 ng/ml) was incubated with baboon peripheral blood mononuclear cells (PBMCs) for 30 minutes before incubating with rhodamine labeled T11. The percentage of rhodamine labeled cells was assessed by flow cytometry (FC) and increased concomitantly to the decrease of the LO-CD2b dose, thereby demonstrating a competition for the CD2 molecule.
Figure 2:
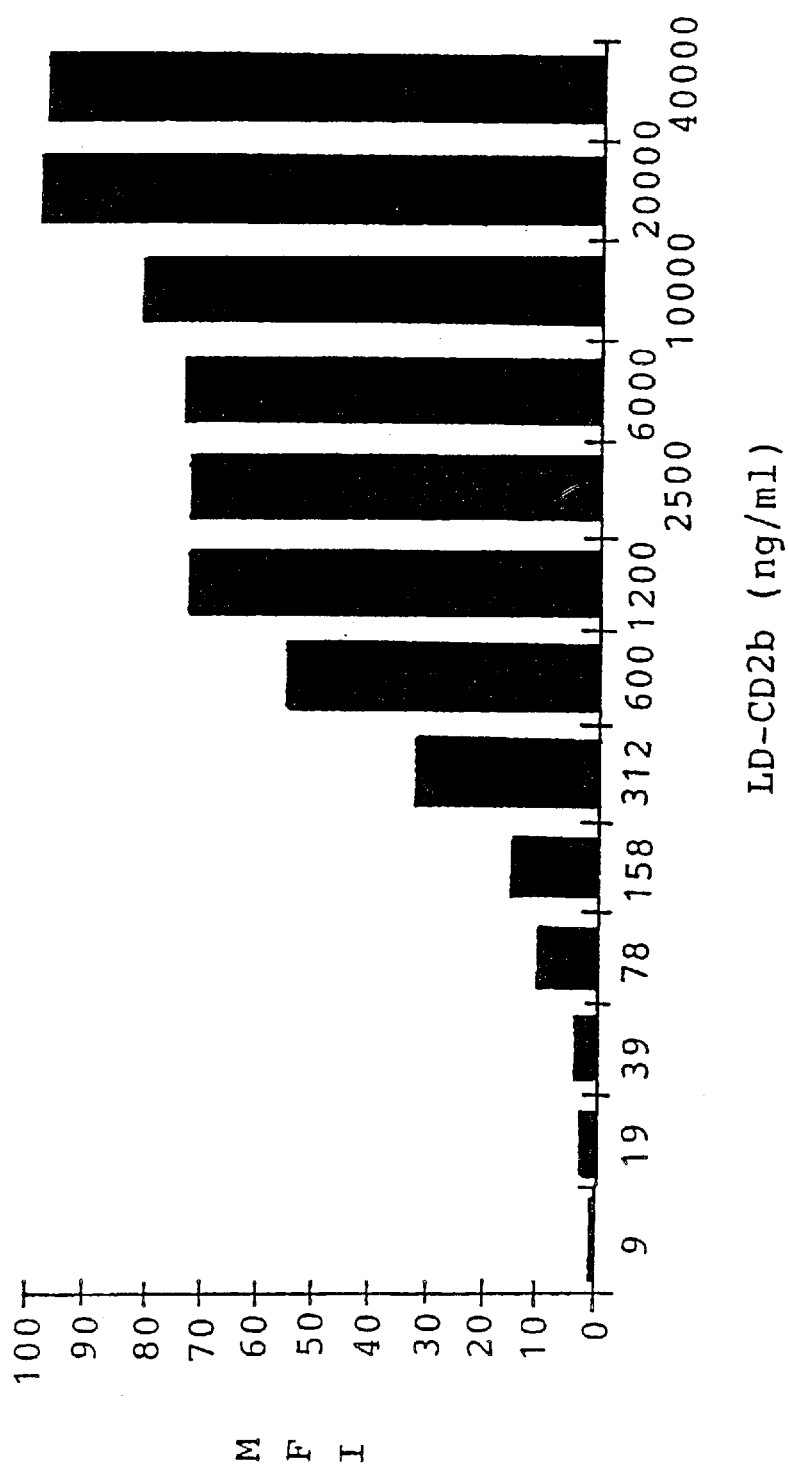
FIG. 2. Mean fluorescence intensity of lymphocytes coated with different LO-CD2b concentrations revealed by a peroxidase-labeled mouse anti-rat mAb (MARG2b). The PBMCs were incubated with different concentrations of LO-CD2b (from 9 ng to 40,000 ng/ml). From a concentration of 9 ng/ml to 20,000 ng/ml, the mean fluorescence intensity (MFI) increased. Above 20,000 ng/ml, the MFI was maximal and stable, evidencing the saturation of the CD2 antigens on baboon PBMCs.
Figure 3A:
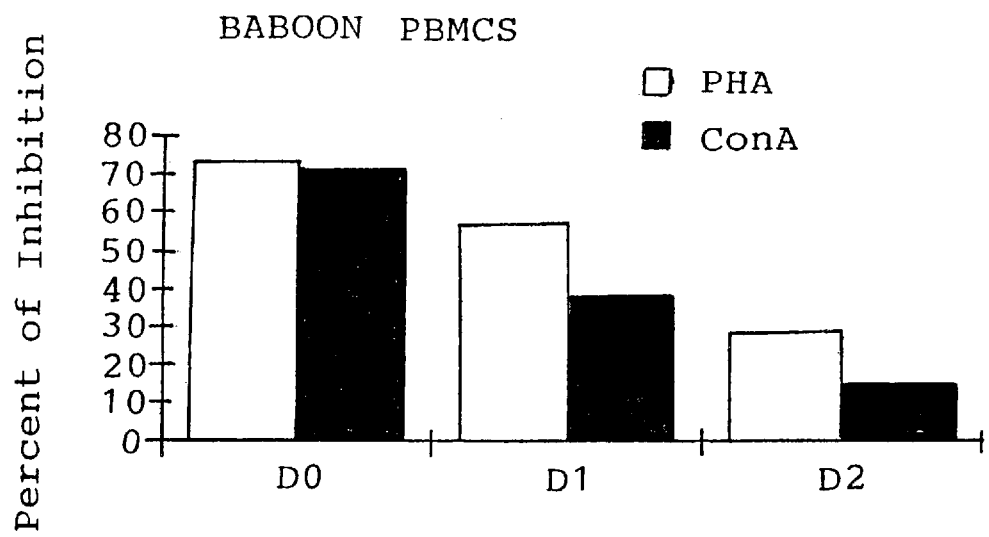
FIG. 3. Effect of LO-CD2b on mitogenic stimulation. Baboon (A) or human (B) PBMC were incubated with phytohemagglutinin (PHA): (1.3 pg/ml) or concanavalin A (ConA) (0.4 μg/ml). LO-CD2b at a concentration of 200 ng/ml was added to the media on day 0, day 1, and day 2 after the beginning of the mitogenic stimulation. Results are obtained from three experiments (mean±SEM) and are the percentage of inhibition of the proliferation resulting from the use of the mitogenic agents. When LO-CD2 was added on the day of MLR initiation, the inhibition of proliferation induced by PHA reached 70% for baboon PBMCs and 60% for human PBMCS. Interestingly, even when added 1 day after the initiatiion of the MLR, there still was a 50% inhibitiion after addition of LO-CD2b. Two days after the beginning of the MLR, LO-CD2b was able to inhibit 15 to 25% of the MLR with both baboon and human PBMCs.
Figure 3B:
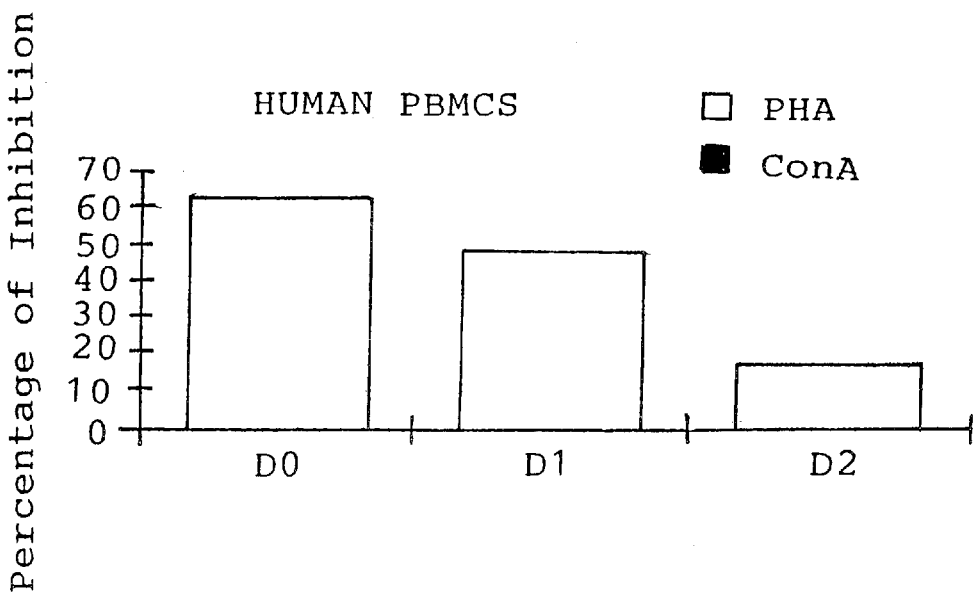
Figure 4A:
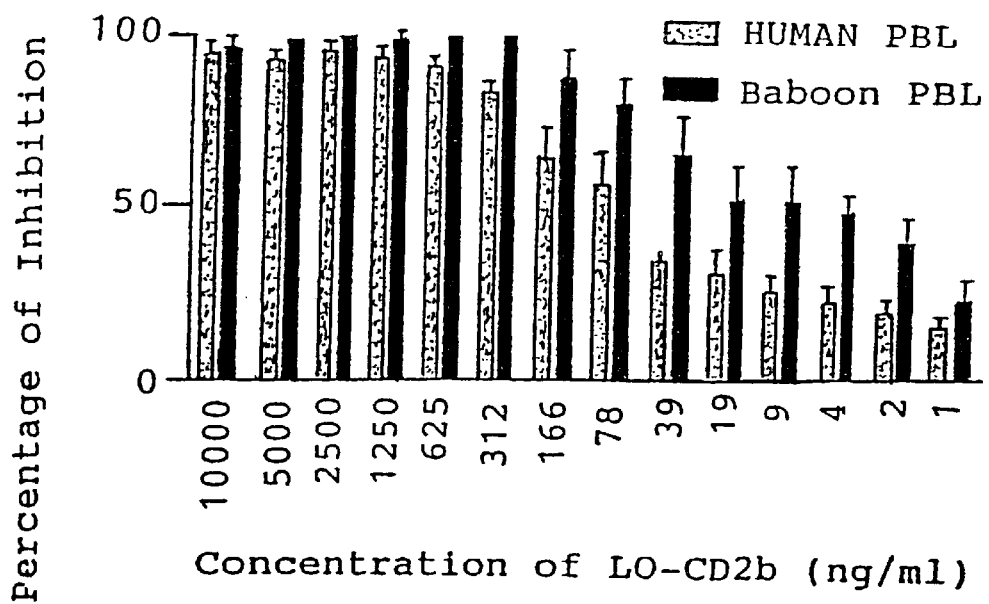
FIG. 4. A. Inhibition of MLR by LO-CD2b. The antibody was added at different concentrations from 10 μg/ml to 600 pg/ml at the beginning of a MLR between two noncompatible baboons or humans for 6 days culture. Between an LO-CD2b concentration of 10,000 and 312 pg/ml, the inhibition of the allogeneic baboon MLR was complete and reached 80 to 90% with human PBMCs. Between an LO-CD2b concentration of 156 and 0.6 ng/ml, the inhibition of the allogeneic MLR decreased progressively with both human and baboon PBMCs.
Figure 4B:
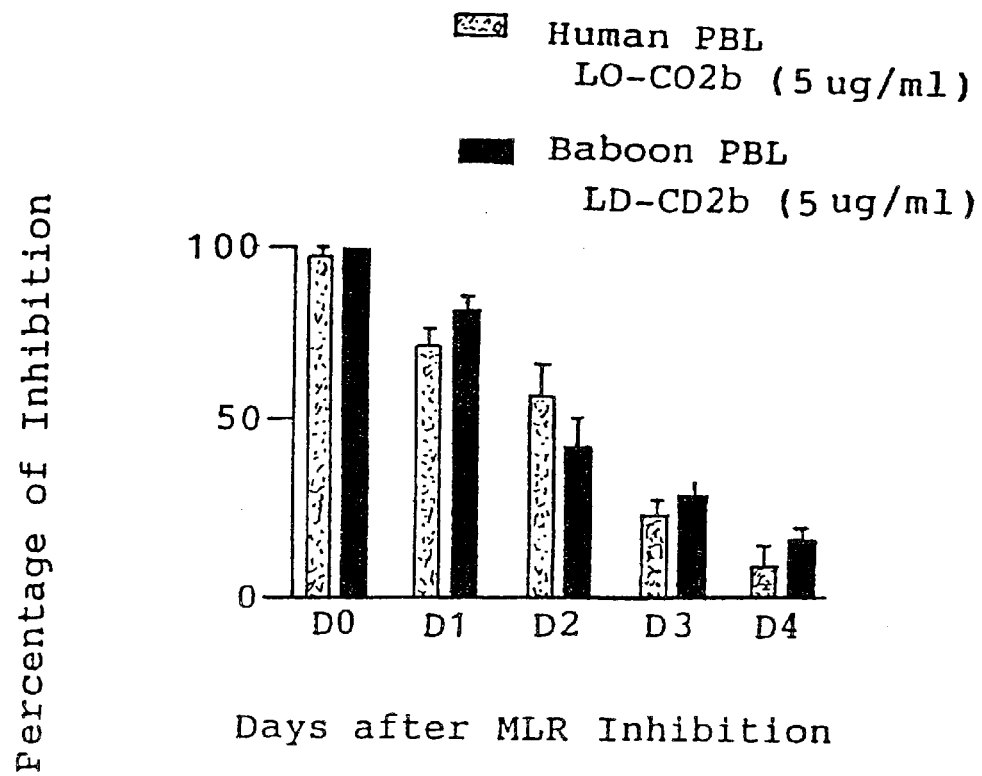
Figure 5A:
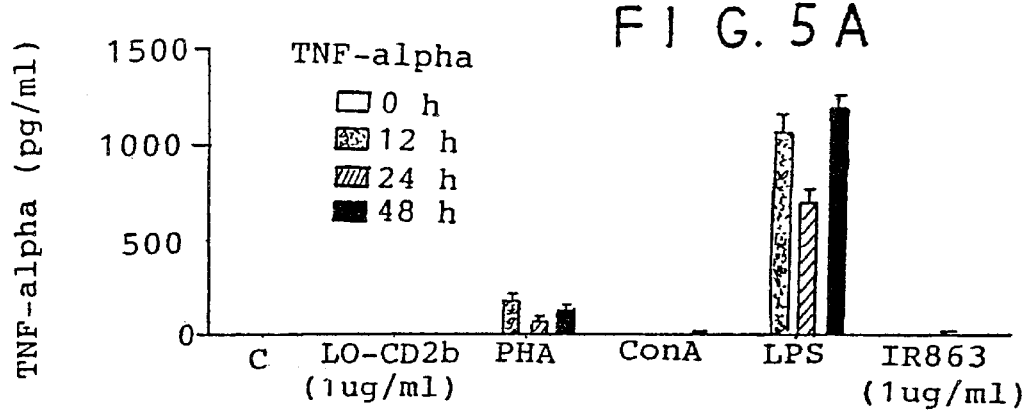
Figure 5B:
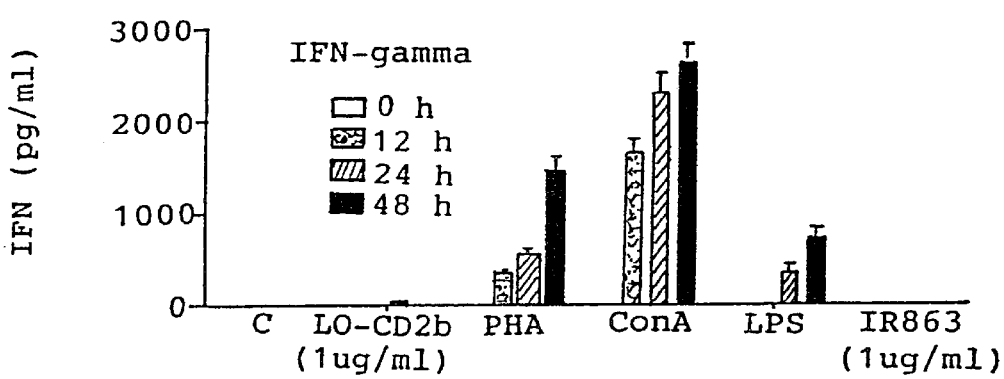
Figure 5C:
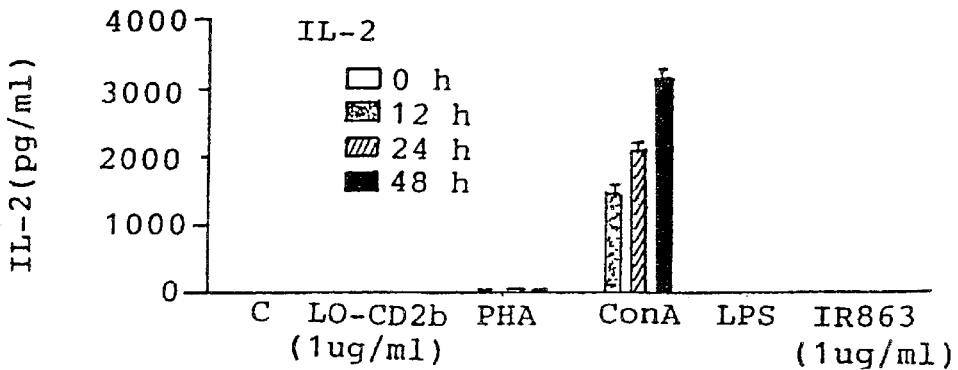

FIG. 5. Effect of LO-CD2b and mitogenic agents on TNF-α (A), IFN-γ (B) and IL-2 (C) release. Baboon PBMC were incubated with LO-CD2b (1 and 0.5 μg/ml), a rat immunocytoma IgG2b isotype IR863 (1 μg/ml) and several mitogenic agents (PHA, ConA and lipopolysaccharide, LPS). Supernatants were taken at 0 h, 12 h, 24 h and 48 h to measure the cytokines release by ELISA (Genzyme). Results were expressed in pg/ml following two experiments. Panel A: The addition of PHA or LPS to the culture produced a significant production of TNF-α, whereas a dose of 1 μg/ml LO-CD2b had no effect. Panel B: The production in vitro of IFN-γ was significant after stimulation by PHA, ConA, and LPS but no IFN-γ release was found after stimulation by LO-CD2b. Panel C: The in vitro release of IL-2 was seen after stimulation by ConA, but not after LO-CD2b stimulation.

Figure 6B:
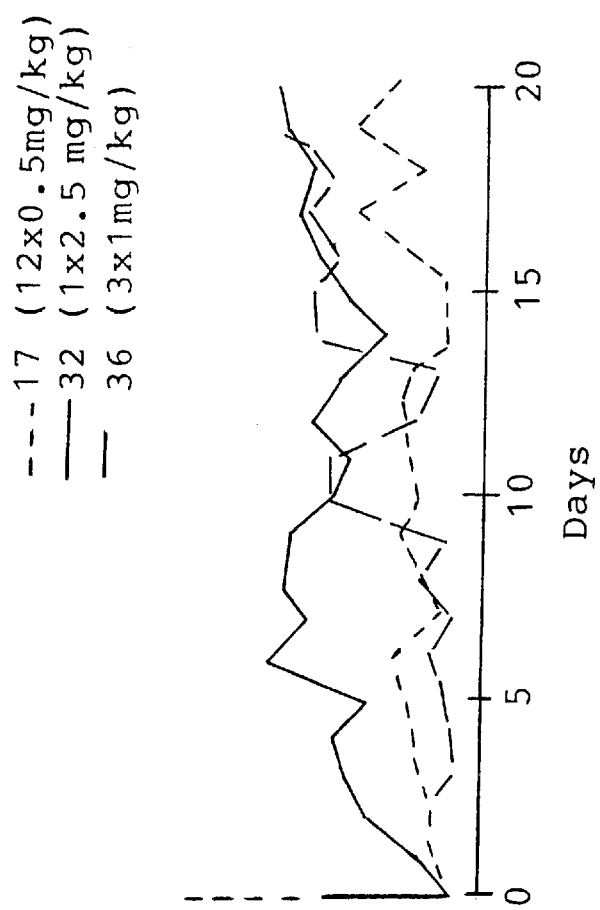
Figure 6A:
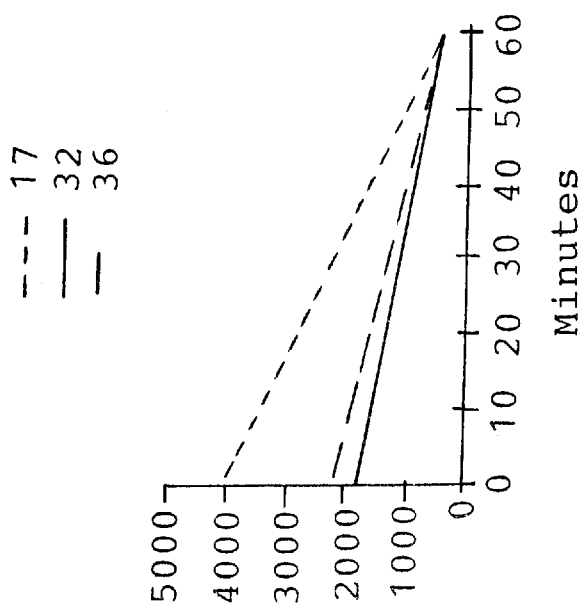

FIG. 6. Panel A: Depletion of total lymphocytes in the peripheral blood during the first hour after LO-CD2b injection. The total count of peripheral lymphocytes dropped >80%. Panel B: Course of lymphocytes in the peripheral blood after one injection of LO-CD2b(baboon 32), three daily injections (baboon 36) and twelve days treatment (baboon 17).

FIG. 7. Comparison of the total circulating lymphocyte count (expressed in % of the pre-treatment value treated with LO-CD2b, ATG (3×50 mg/kg), Total Body Irradiation (TBI, 3 Gy) with or without LO-CD2b. LO-CD2b alone produced a rapid (within one hour) and strong (>80%) in vivo depletion for almost two weeks. In contrast, a three-day regimen of ATG at 50 mg/kg did not provide a significant T-cell depletion. TBI alone or concomitant with a three-day regimen of LO-CD2b provoked a more durable peripheral T-cell depletion.

Figure 8:
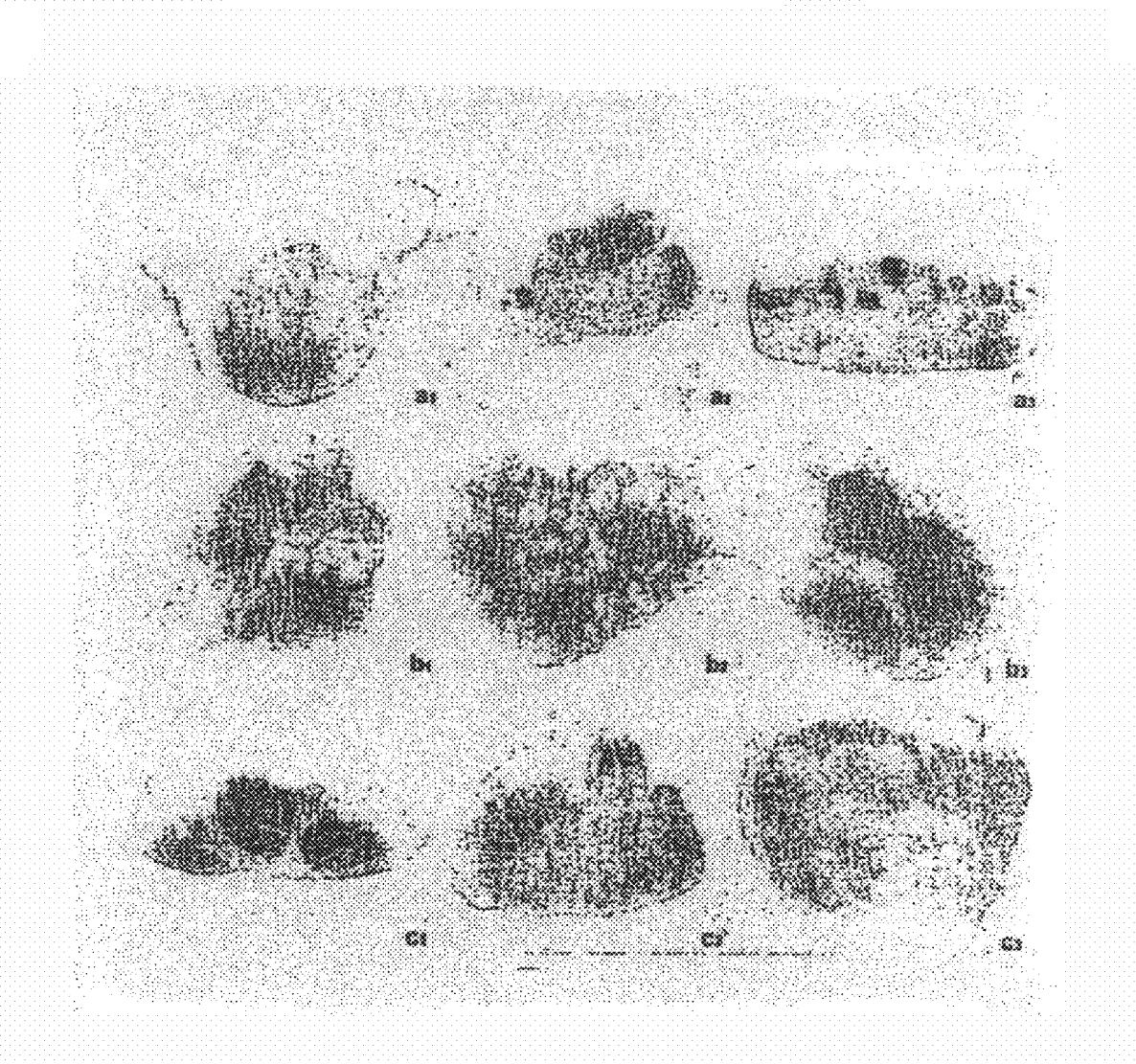

FIG. 8. Immunohistology of baboon inguinal lymph nodes. The lymph nodes were labeled with peroxidized anti-CD3 mAb to stain the T-lymphocytes and colored by hematoxylin and eosin. Panel A: TBI (3 Gy) provided a T-cell depletion seven (a2) to ten (a3) days after treatment. Panel B: In comparison, a three-day regimen of LO-CD2b at 2 mg/kg resulted in a partial depletion of lymph node T-cells, seven days (b2) after the beginning of the treatment (b1:pre-treatment lymph node T-cells) and (b3) ten days after treatment. Panel C: The combination of both TBI and LO-CD2b treatment resulted in a slightly higher level of T-cell depletion than TBI alone.

Figure 9:
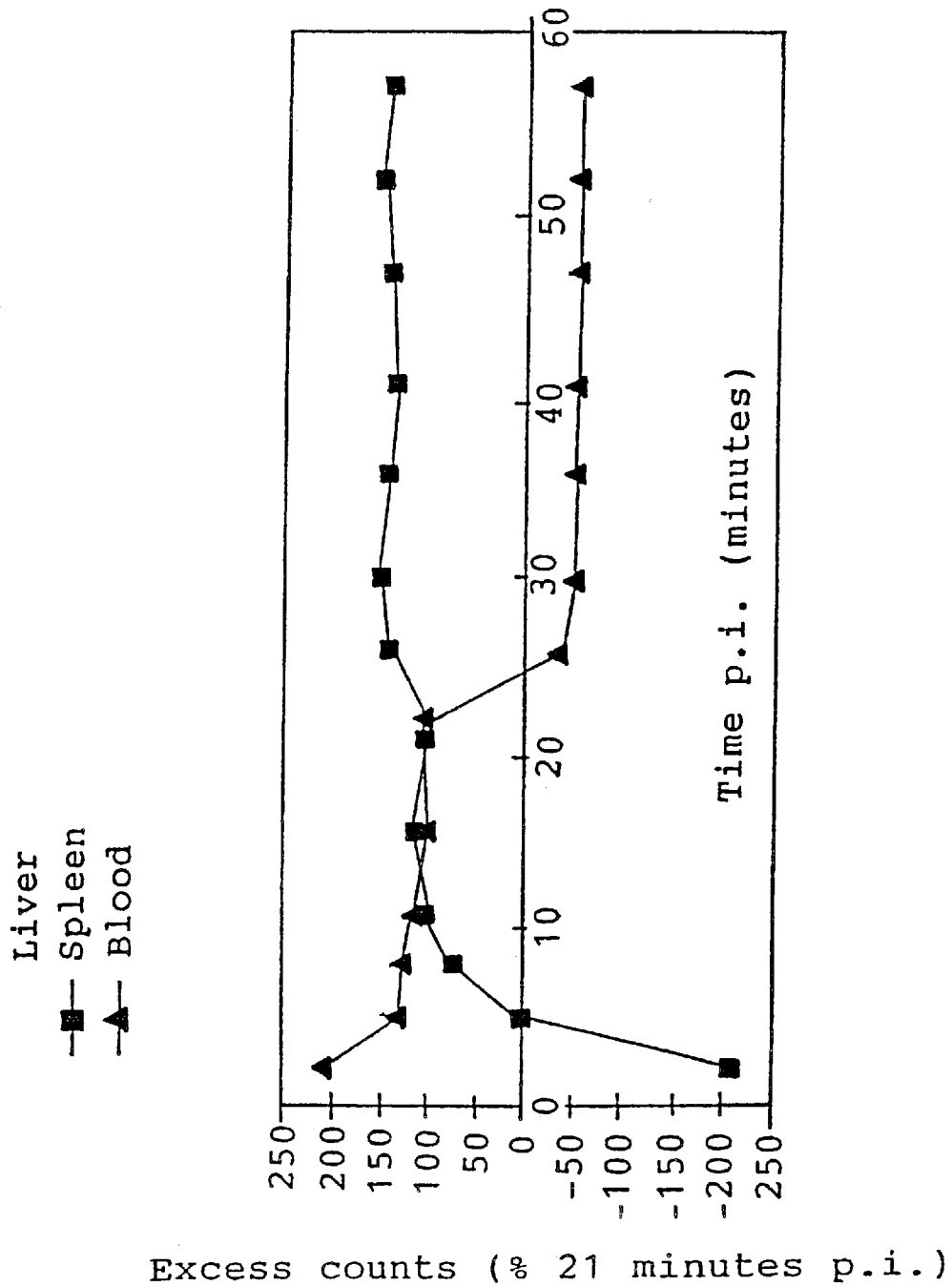

FIG. 9. Indium Scanning. Excess counts, expressed as the percentage of the value at 21 minutes (time of LO-CD2b (2.5 mg/kg) injection) represents the activity which was detected in liver, spleen, and peripheral blood. As illustrated in this figure, the excess count increased in both liver and spleen after LO-CD2b single injection whereas counts decreased in the peripheral blood. This result suggests a massive capture of labeled lymphocytes in the reticulo-endothelial system of these organs.

FIG. 10. Inhibition of xenogeneic MLR by LO-CD2b. The mAb was added at 200 and 20 ng/ml at the beginning of a MLR between baboon #49 PBMC and three different Belgian large white pigs PBMC whereas the proliferation was high in presence of IR 863 (control antibody) at the same concentration.

Figure 11:
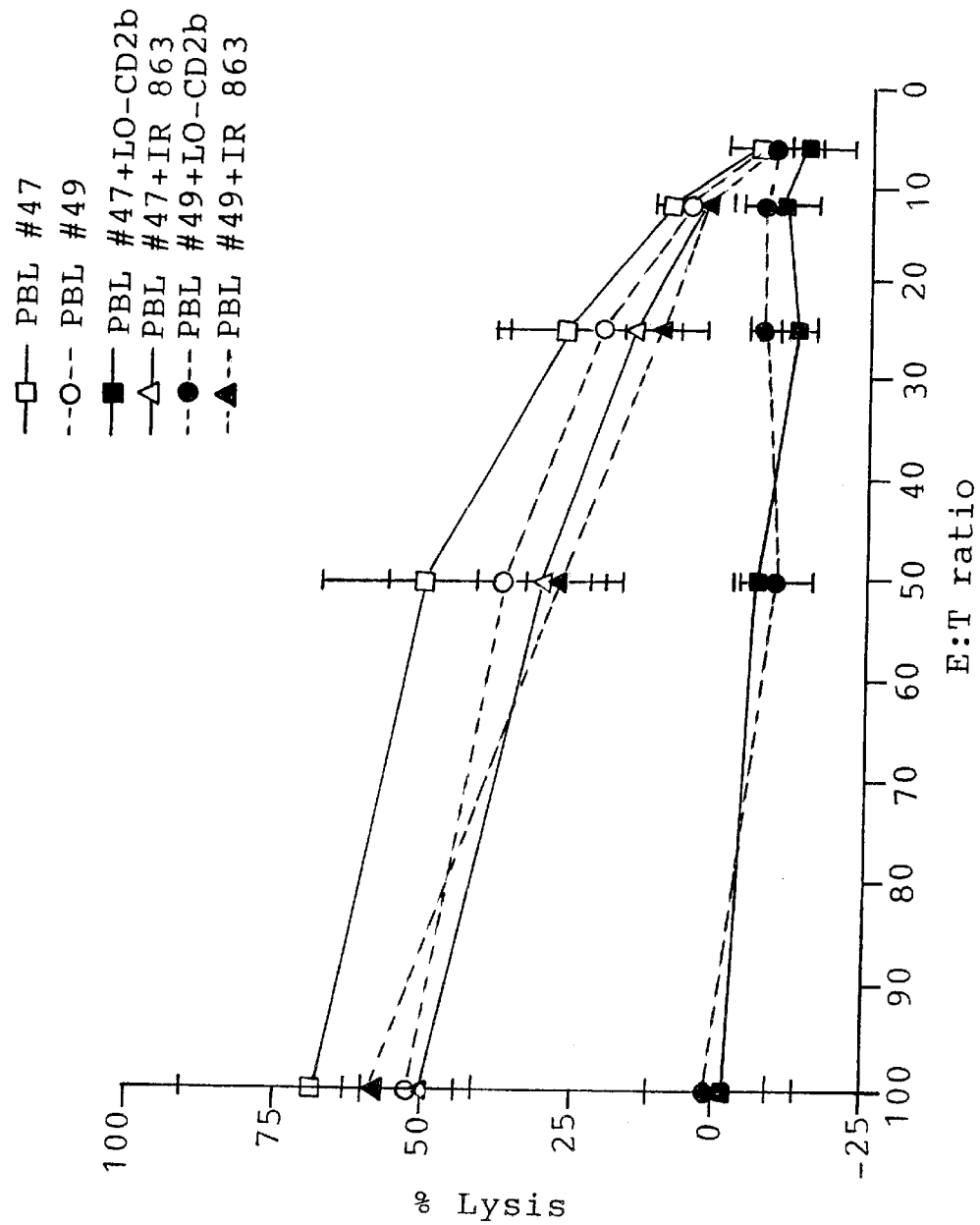

FIG. 11. Unprimed baboon peripheral blood lyphocytes (PBLs) were used to measure cytotoxicity activity against K562 cells. Baboon PBMC were used alone (Baboon#47: open square; Baboon#49: open circle), after a 2 hours incubation with 200 ng/ml of LO-CD2b (Baboon#47: filled square; baboon#49: filled circle) or of IR 863 (control antibody) (Baboon#47: open triangle; baboon#49: filled triangle). Cytotoxicity of the PBL is expressed as % specific lysis at different effector/target ratios. Results were expressed following 3 experiments.

Figure 12:
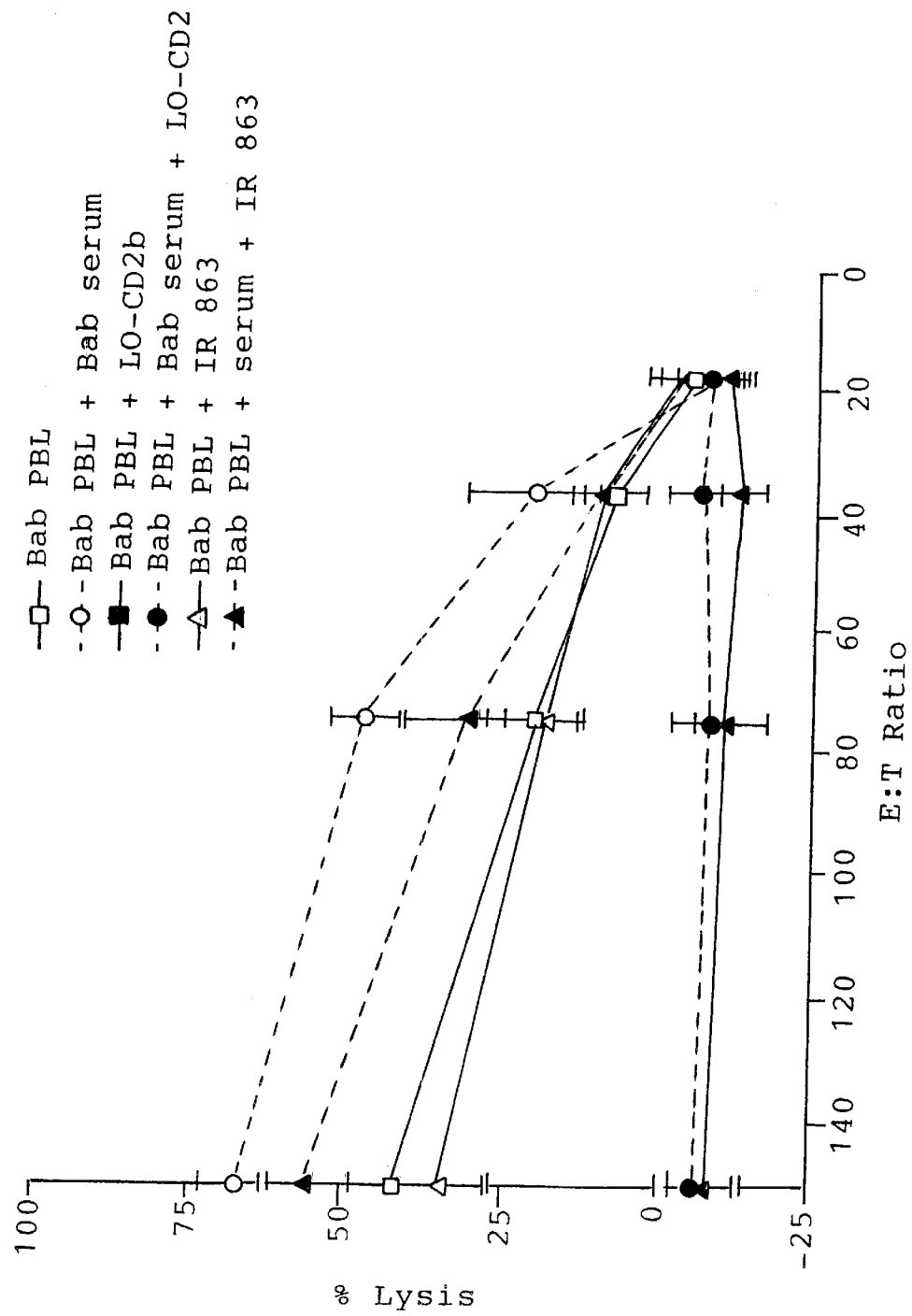

FIG. 12. Unprimed baboon PBL were used to measure cytotoxicity activity against porcine aortic endothelial cells (PAEC). Baboon PBL were used alone against PAEC (Open square) or against incubated PAEC with baboon serum (1/2 hour) (Open circle). Baboon PBL incubated 2 hours with LO-CD2b (200 ng/ml) were used against PAEC incubated with (filled circle) or without (filled square) baboon serum. As control, baboon PBL incubated with 200 ng/ml of IR 863 were used against PAEC incubated (filled triangle) or without (Open triangle) baboon serum. Cytotoxicity of the PBL is expressed as % specific lysis at different effector/target ratios. Results were expressed following 5 experiments.

Figure 13:
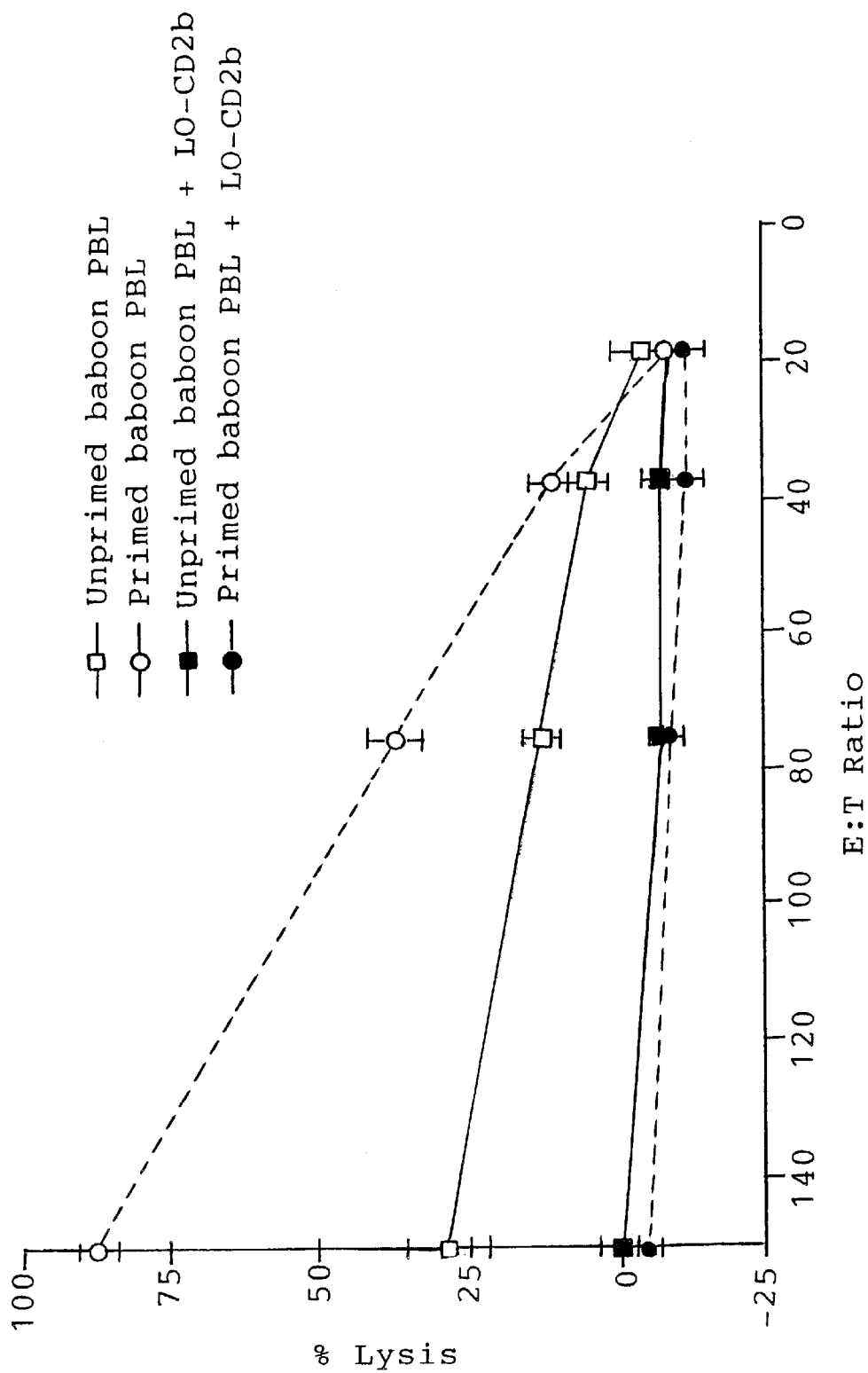

FIG. 13. Anti-porcine cytotoxicity of unprimed baboon PBL incubated (filled square) or not (open square) with LO-CD2b (200 ng/ml) were assessed in comparison of anti-porcine cytotoxicity of primed baboon PBL incubated (filled circle) or not (open circle) with LO-CD2b. Cytotoxicity of the PBL is expressed as % specific lysis at different effector/target ratios. Results were expressed following 3 experiments.

TABLE 1. Experimental groups

TABLE: 2. Peripheral level of lymphocytes (/μl) before and after LO-CD2b treatment.

TABLE 3. Percentage and mean fluorescence intensity assessed at FC for CD2+, CD2+ and CD16+/CD2+ cells in peripheral blood before treatment (D0) and at days 3, 7, 10, 14 and 20 and in lymph node at D0, 7 and 10 in baboons 43 and 15.

TABLE 4. Count of lymphocytes recovered from inguinal lymph nodes at different days after the beginning of the treatment.

TABLE 5. CH50 and AH50 values for two baboons injected with 2.5 mg/kg (Bab#32) and 0.5 mg/kg iv LO-CD2b mAb. The serum samples were taken before, at 0.5 hour, and one hour after the injection. No activation of the classical or alternate pathways of the complement system was observed.

TABLE 6. Viability of baboon PBMC and PBL before and after a 2 hour LO-Cd2b (200 ng/ml) incubation.

TABLE 7. $CD_2$ and CD16+/CD2+ cells relative percentage (%) estimated in peripheral blood by flow cytometry at DO (before LO-Cd2b treatment) and at days 1, 7, and 14 after injections.

TABLE 1

| Group | Baboon Number | Treatment | Frequency & Dosage | Survival Days |
|---|---|---|---|---|
| Group 1 | 11 | LO-CD2b | 1 × 0.45 mg/kg | — |
| (single of | 14 | LO-CD2b | 1 × 1 mg/kg | — |
| muitiple | 32 | LO-CD2b | 1 × 2.5 mg/kg | — |
| LO-CD2b | 17 | LO-CD2b | 12 × 0.5 mg/kg | — |
| intravenous | 35 | LO-CD2b | 3 × 0.5 mg/kg | — |
| injections) | 36 | LO-CD2b | 3 × 1 mg/kg | — |
|  | 42 | LO-CD2b | 3 × 2 mg/kg | — |
| Group 2 | 23 | LO-CD2b | 12 × 0.35 mg/kg | 20 |
| (LO-CD2b | 25 | LO-CD2b | 12 × 0.25 mg/kg | 15 |
| treatment and renal group) |  |  |  |  |
| Group 3 | 15 | no | — | 10 |
| (Control) | 39 | ATG | 3 × 50 mg/kg |  |
|  | 33 | Irradiation | 2 × 1.5 Gy |  |
|  | 44 | Irradiation and LO-CD2b | 2 × 1.5 Gy 3 × 2 mg/kg |  |

TABLE 2

| Baboons & doses of LO-CD2b | D0 | 1 hr | D1 | D2 | D3 | D7 | D10 | D15 | d20 | d30 |
|---|---|---|---|---|---|---|---|---|---|---|
| 11 (1 × 0.045 mg/kg) | 1700 | 700 | 0 | ND | ND | ND | ND | ND | ND | ND |
| 14 (1 × 1 mg/kg) | 2900 | 200 | 0 | 2200 | 1400 | 3700 | 2700 | 3200 | ND | ND |
| 32 (1 × 2.5 mg/kg) | 1770 | 400 | 830 | 1560 | 2041 | 2400 | 2100 | 1335 | ND | 3280 |
| 35 (3 × 0.5 mg/kg) | 1640 | 340 | 680 | 600 | 1410 | 590 | 930 | 1140 | 930 | 1700 |
| 36 (3 × 1 mg/kg) | 2220 | 370 | 570 | 760 | 350 | 330 | 4240 | 2350 | 1250 | ND |
| 42 (3 × 2 mg/kg) | 2520 | 260 | 510 | 520 | 800 | 650 | 570 | 1670 | 2490 | ND |
| 17 (12 × 0.5 mg/kg) 23 (12 × /kg) | 4100 | 300 | 1000 | 800 | 900 | 600 | 900 | 500 | 1300 | ND |

TABLE 2-continued

| Baboons & doses of LO-CD2b | D0 | 1 hr | D1 | D2 | D3 | D7 | D10 | D15 | d20 | d30 |
|---|---|---|---|---|---|---|---|---|---|---|
| 23 (12 × 0.35 mg/kg) | 3200 | ND | 700 | 400 | 800 | 0 | 0 | 0 | 0 | 0 |
| 25 (12 × 0.25 mg/kg) | 3100 | ND | 0 | 400 | 600 | 0 | 200 | 1100 | ND | ND |
| 15 | 3500 | ND | 2000 | 2800 | 2400 | 2300 | 3300 | ND | ND | ND |
| 39 ATG | 1500 | 150 | 560 | ND | 680 | 1060 | 2900 | 2190 | 1400 | ND |
| 33 Irradiation | 2030 | 1800 | 1060 | 320 | 300 | 270 | 220 | 370 | 630 | 2520 |
| 44 Irradiation and LO-CD2b | 5440 | 11101 350 | 280 | 130 | 330 | 170 | 280 | ND | ND | |

TABLE 3

| Baboons | CD | Peripheral Blood | | | | | | Lymph Node | | |
|---|---|---|---|---|---|---|---|---|---|---|
| | | D0 | D3 | D7 | D10 | D14 | D20 | D0 | D7 | D10 |
| 42 | CD2 | | | | | | | | | |
| LO-CD2b (3 × 2 mg/kg) | % | 85 | 0 | 12 | 25 | 43.5 | 57 | 94 | 28 | 89 |
| | MFI | 264 | 0 | 3 | 181 | 227 | 362 | 106 | 38 | 119 |
| | CD20 | | | | | | | | | |
| | % | 9.2 | 39.2 | 23.3 | 13.1 | 31.4 | 14.7 | 5.5 | 12.9 | 0.1 |
| | MFI | 133 | 170 | 117 | 119 | 91 | 147 | 135 | 147 | 130 |
| | CD16+/CD2+ | | | | | | | | | |
| | % | 2.9 | 0 | 0.1 | 3.2 | 4.3 | 0.1 | 0 | 0.1 | |
| | MFI | 259 | 0 | 33 | 104 | 66 | 33 | 45 | 47 | 69 |
| 15 Control Animal | CD2 | | | | | | | | | |
| | % | 80 | ND | 64 | ND | 63 | ND | 57 | ND | 65 |
| | MFI | 77 | ND | 173 | ND | 160 | ND | 30.2 | ND | 173 |
| | CD20 | | | | | | | | | |
| | % | 30 | ND | 20 | ND | 30 | ND | 17 | ND | 22 |
| | MFI | 385 | ND | 1806 | ND | 1300 | ND | 145 | ND | 1938 |
| | CD16+/CD2+ | | | | | | | | | |
| | % | 5.9 | ND | 2.5 | ND | 0.3 | ND | 0.3 | ND | 3 |
| | MFI | 113 | ND | 160 | ND | 180 | ND | 34.8 | ND | 255 |

TABLE 4

| Baboon Number | D0 | D7 | D10 | Treatment |
|---|---|---|---|---|
| 35 | 460 000 | 670 000 | 610 000 | LO-CD2b (3 × 0.5 mg/kg) |
| 36 | 247 000 | 75 000 | 333 000 | LO-CD2b (3 × 1 mg/kg) |
| 42 | 3 200 000 | 1 000 000 | 3 000 000 | LO-CD2b (3 × 2 mg/kg) |
| 39 | 666 000 | 970 000 | 600 000 | ATG (3 × 50 mg/kg) |
| 33 | 780 000 | 360 000 | 420 000 | Irradiation (2 × 1.5 Gy) |
| 44 | 732 000 | 256 000 | 268 000 | Irradiation (2 × 1.5 Gy) and LO-CD2b (3 × 2 mg/kg) |

TABLE 5

| | Bab 35 | | Bab 32 | |
|---|---|---|---|---|
| | Classical Path* | Alternative Path** | Classical Path* | Alternative Path** |
| D0 | 43.2 | 27.2 | 74.5 | 46.1 |
| D1/2h | 46.8 | 26.7 | 78.0 | 44.0 |
| D1h | 31.5 | 26.3 | 76.1 | 45.1 |

*Human normal range: 30 to 50 U; **28 to 144 U

TABLE 6

| Cells | % PI positive cells | % blue trypan positive cells | % MARG2b positive cells |
|---|---|---|---|
| PBMC alone | 2.5 | 1.6 | 3.7 |
| PBMC + LO-CD2b | 3.0 | 2.1 | 86.1 |

TABLE 6-continued

| Cells | % PI positive cells | % blue trypan positive cells | % MARG2b positive cells |
|---|---|---|---|
| PBL alone | 13.6 | 8.0 | 1.5 |
| PBL + LO-CD2b | 14.0 | 8.7 | 71.7 |

TABLE 7

| Baboon Number | CD | D0 | D1 | D7 | D14 | Treatment |
|---|---|---|---|---|---|---|
| 15 | CD2$^+$ | 80 | 60 | 57 | 65 | No |
|  | CD2$^+$/CD16$^+$ | 6.1 | 5.6 | 6.0 | 3.9 |  |
| 17 | CD2$^+$ | 84.9 | 1.2 | 1.2 | 14.1 | LO-CD2b |
|  | CD2$^+$/CD16$^+$ | 10.1 | 1.2 | 1.2 | 6.4 | (12 × 0.5 mg/kg) |
| 25 | CD2$^+$ | 73 | 2.1 | 7.8 | 18.3 | LO-CD2b |
|  | CD2$^+$/CD16$^+$ | 8.4 | 0.3 | 0.5 | 4.6 | (12 × 0.25 mg/kg) |
| 32 | CD2$^+$ | 67.5 | 5.6 | 17.8 | 29 | LO-CD2b |
|  | CD2$^+$/CD16$^+$ | 21.8 | 2.3 | 10.8 | 19.1 | (1 × 2.5 mg/kg) |
| 35 | CD2$^+$ | 60.1 | 3.5 | 1.2 | 36.7 | LO-CD2b |
|  | CD2$^+$/CD16$^+$ | 6.1 | 0.1 | 0.4 | 4.2 | (3 × 0.5 mg/kg) |
| 36 | CD2$^+$ | 87.4 | 8.5 | 23.4 | 36.7 | LO-CD2b |
|  | CD2$^+$/CD16$^+$ | 12.9 | 1.0 | 6.8 | 12.0 | (2 × 1 mg/kg) |

What is claimed is:

1. An antibody produced by the cell line deposited as ATCC PTA-802.

2. The cell line deposited as ATCC PTA-802.

* * * * *